(12) United States Patent
Schaffer et al.

(10) Patent No.: US 8,163,893 B2
(45) Date of Patent: Apr. 24, 2012

(54) PSEUDOTYPED RETROVIRAL VECTORS AND METHODS OF USE THEREOF

(75) Inventors: David V. Schaffer, Pleasant Hill, CA (US); Julie H. Yu, Berkeley, CA (US)

(73) Assignee: The Regents of the University of Caifornia, Oakland, CA (US)

( * ) Notice: Subject to any disclaimer, the term of this patent is extended or adjusted under 35 U.S.C. 154(b) by 363 days.

(21) Appl. No.: 12/279,171

(22) PCT Filed: Feb. 13, 2007

(86) PCT No.: PCT/US2007/003724
§ 371 (c)(1),
(2), (4) Date: Feb. 5, 2009

(87) PCT Pub. No.: WO2007/095201
PCT Pub. Date: Aug. 23, 2007

(65) Prior Publication Data
US 2009/0220458 A1   Sep. 3, 2009

Related U.S. Application Data

(60) Provisional application No. 60/774,141, filed on Feb. 15, 2006.

(51) Int. Cl.
*C07H 21/04* (2006.01)
*C12N 15/00* (2006.01)
*A01N 63/00* (2006.01)

(52) U.S. Cl. .................. 536/23.4; 536/23.72; 435/320.1

(58) Field of Classification Search .................. None
See application file for complete search history.

(56) References Cited

U.S. PATENT DOCUMENTS

| | | | |
|---|---|---|---|
| 5,739,018 | A | 4/1998 | Miyanohara et al. |
| 5,817,491 | A | 10/1998 | Yee et al. |
| 6,133,027 | A | 10/2000 | Yee et al. |
| 6,432,705 | B1 | 8/2002 | Yee et al. |
| 7,347,998 | B2 * | 3/2008 | Hall et al. ............ 424/93.2 |
| 7,608,449 | B2 * | 10/2009 | McCray et al. ........ 435/320.1 |

FOREIGN PATENT DOCUMENTS

| | | |
|---|---|---|
| WO | WO9960110 | 11/1999 |
| WO | WO 00/55335 * | 9/2000 |
| WO | WO04000220 | 12/2003 |
| WO | WO2004022716 | 3/2004 |
| WO | WO2004026338 | 4/2004 |

OTHER PUBLICATIONS

Azzouz et al. VEGF delivery with retrogradely transported lentivector prolongs survival in a mouse ALS model. (2004) Nature 429:413-417.

Guibinga et al. Ligand-modified vesicular stomatitis virus glycoprotein displays a temperature-sensitive intracellular trafficking and virus assembly phenotype. (2004) Molec. Therapy 9:76-84.

Parrott et al. Metabolically biotinylated adenovirus for cell targeting, ligand screening, and vector purification. (2003) Mol. Ther. 8:688-700.

Schlehuber and Rose. Prediction and identification of a permissive epitope insertion site in the vesicular stomatitis virus glycoprotein. (2004) J. Virol. 78:5079-5087.

Wong et al. Transduction patterns of pseudotyped lentiviral vectors in the nervous system. (2004) Molec. Therapy 9:101-111.

Ye, et al. Tagging retrovirus vectors with a metal binding peptide and one-step purification by immobilized metal affinity chromatography. J Virol. Sep. 2004;78(18):9820-7.

Gupta, et al. Immunogenic and antigenic properties of recombinant soluble glycoprotein of rabies virus. Vet Microbiol. Jul. 1, 2005;108(3-4):207-14.

Alonso, et al. The NV gene of snakehead rhabdovirus (SHRV) is not required for pathogenesis, and a heterologous glycoprotein can be incorporated into the SHRV envelope. J Virol. Jun. 2004;78(11):5875-82.

Li et al. Mutational analysis of the vesicular stomatitis virus glycoprotein G for membrane fusion domains. Journal of Virology, 1993, vol. 67, No. 7, pp. 4070-4077.

Schlehuber L. et al., "Prediction and Identification of a Permissive Epitope Insertion Site in the Vesicular Stomatitis Virus Glycoprotein" *Journal of Virology*, 78(10):5079-5087 (2004).

Yu J. et al., "Selection of Novel Vesicular Stomatitis Virus Glycoprotein Variants from a Peptide Insertion Library for Enhanced Purification of Retroviral and Lentiviral Vectors" Journal of Virology, 80(7):3285-3292 (2006).

Coil, et al. "Phosphatidylserine is Not the Cell Surface Receptor for Vesicular Stomatitis Virus", Journal of Virology, Oct. 2004, vol. 78, No. 20, p. 10920-10926.

Dreja, et al. "The Effects of N-terminal inserSV-G of an scFv Peptide", Virology Journal, Sep. 2006, vol. 3, No. 69, p. 1-8.

Roche, et al. "Crystal Structure of the Low-pH Form of the Vesicular Stomatitis Virus Glycoprotein G", Science, Jul. 2006, vol. 313, p. 187-191 and p. 1387-1389.

Roche, et al. "Structure of the Prefusion Form of the Vesicular Stomatis Virus Glycoprotein G", Science, vol. 35, p. 843-848, 2007.

* cited by examiner

*Primary Examiner* — Quang Nguyen
(74) *Attorney, Agent, or Firm* — Paula A. Borden; Bozicevic, Field & Francis LLP.

(57) ABSTRACT

The present invention provides nucleic acids encoding recombinant envelope proteins; and packaging cells comprising the nucleic acids, which packaging cells provide for encapsidation of recombinant retroviral vectors. The present invention provides producer cells that produce pseudotyped recombinant retroviral vectors. The present invention further provides methods of purifying pseudotyped recombinant retroviral vectors; and purified pseudotyped recombinant retroviral vectors. The present invention further provides methods of delivering a gene product to an individual. The methods generally involve introducing a subject recombinant retroviral vector into an individual.

13 Claims, 8 Drawing Sheets

FIG. 1A
FIG. 1B
His$_6$ insert:
X$_1$ X$_2$ A A H H H H H H G A A
NNN NNT GCG GCC CAC CAC CAC CAT CAT CAT GGG GCC GCA
FIG. 1C
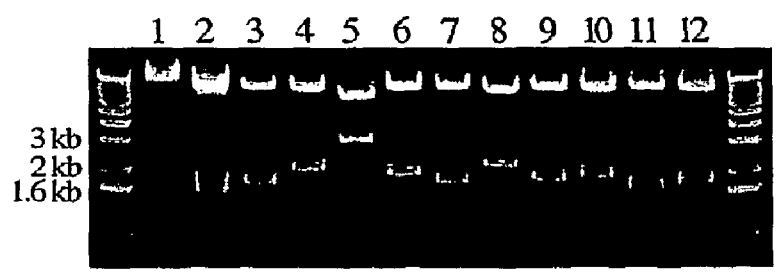

FIG. 3A vsv-g-his₆ library + gag-pol wt vsv-g

↓ +doxycycline transfect viral library package with WT VSV-G harvest viral library infect gag-pol expressing cells select for replication and Ni-NTA binding

FIG. 3B

☐ WT VSV-G
▧ VSV-G-His$_6$ y-axis: titer (IU/ml), 1E+3 to 1E+7
x-axis: round of selection, 1 2 3

MKCFLYLAFLFIGVNCKFTIVFPHNQKGNWKNVPSNYHYCPSSS
DLNWHNDLIGTGLQVKMPKSHKAIQADGWMCHASKWVTTCDFRWYGPKYITHSIRSFT
PSVEQCKESIEQTKQGTWLNPGFPPQSCGYATVTDAEAVIVQVTPHHVLVDEYTGEWV
DSQFINGKCSNDICPTVHNSTTWHSDYKVKGLCDSNLISTDITFFSEDRELSSLGKEG
TGFRSNYFAYETGDKACKMQYCKHWGVRLPSGVWFEMADKDLFAAARFPECPEGSSIS
APSQTSVDVSLIQDVERILDYSLCQETWSKIRAGLPISPVDLSYLAPKNPGTGPAFTI
INGTLKYFETRYIRVDIAAPILSRMVGMISGTTTERELWDDWAPYEDVEIGPNGVLRT
SSGYKFPLYMIGHGMLDSGLHLSSKAQVFEHPHIQDAASQLPDDEILFFGDTGLSKNP
IDFVEGWFSSWKSSIASFFFIIGLIIGLFLVLRVGIYLYIKLKHTKKRQIYTDIEMNR
LGR (SEQ ID NO:1)

FIG. 6B

```
   1 aacagagatc gatctgtttc cttgacacca tgaagtgctt tttgtactta gcttttttat
  61 tcatcggggt gaattgcaag ttcaccatag tttttccaca caaccaaaaa ggaaactgga
 121 aaaatgttcc ttccaattac cattattgcc cgtcaagctc agatttaaat tggcataatg
 181 acttaatagg cacaggctta caagtcaaaa tgcccaagag tcacaaggct attcaagcag
 241 acggttggat gtgtcatgct tccaaatggg tcactacttg tgatttccgc tggtacggac
 301 cgaagtatat aacacattcc atccgatcct tcactccatc tgtagaacaa tgcaaggaaa
 361 gcattgaaca aacgaaacaa ggaacttggc tgaatccagg cttccctcct caaagttgtg
 421 gatatgcaac tgtgacggat gccgaagcag tgattgtcca ggtgactcct caccatgtgc
 481 ttgttgatga atacacagga gaatggttg attcacagtt catcaacgga aaatgcagca
 541 atgacatatg ccccactgtc cataactcca caacctggca ttccgactat aaggtcaaag
 601 ggctatgtga ttctaacctc atttccacgg acatcacctt cttctcagag gacagagagc
 661 tatcatccct aggaaaggag ggcacagggt tcagaagtaa ctactttgct tatgaaactg
 721 gagacaaggc ctgcaaaatg cagtactgca agcattgggg agtcagactc ccatcaggtg
 781 tctggttcga gatggctgat aaggatctct ttgctgcagc cagattccct gaatgcccag
 841 aagggtcaag tatctctgct ccatctcaga cctcagtgga tgtaagtctc attcaggacg
 901 ttgagaggat cttggattat tccctctgcc aagaaacctg gagcaaaatc agagcgggtc
 961 ttcccatctc tccagtggat ctcagctatc ttgctcctaa aaacccagga accggtcctg
1021 cctttaccat aatcaatggt accctaaaat actttgagac cagatacatc agagtcgata
1081 ttgctgctcc aatcctctca agaatggtcg gaatgatcag tggaactacc acagaaaggg
1141 aactgtggga tgactgggct ccatatgaag acgtggaaat tggacccaat ggagttctga
1201 ggaccagttc aggatataag tttcctttat atatgattgg acatggtatg ttggactccg
1261 gtcttcatct tagctcaaag gctcaggtgt ttgaacatcc tcacattcaa gacgctgctt
1321 cgcagcttcc tgatgatgag atttttatttt tggtgatac tgggctatcc aaaaatccaa
1381 tcgactttgt cgaaggttgg ttcagtagtt ggaagagctc cattgcctct ttttttcttta
1441 tcataggtt aatcattgga ctattcttgg ttctccgagt tggtatttat ctttacatta
1501 aattaaagca caccaagaaa agacagattt atacagacat agagatgaac cgacttggaa
1561 ggtaactcaa atcctgcaca acagattctt catgtttgga ccaaatcaac ttgtgatacc
1621 atgctcaaag aggcctcaat tatatttgag ttttaatttt ttatg (SEQ ID NO:2)
```

FIG. 6C

MKCLLYLAFLFIGVNCKFTIVFPHNQKGNWKNVPSNYHYCPSSS

DLNWHNDLIGTALQVKMPKSHKAIQADGWMCHASKWVTTCDFRWYGPKYITHSIRSFT

PSVEQCKESIEQTKQGTWLNPGFPPQSCGYATVTDAEAVIVQVTPHHVLVDEYTGEWV

DSQFINGKCSNYICPTVHNSTTWHSDYKVKGLCDSNLISMDITFFSEDGELSSLGKEG

TGFRSNYFAYETGGKACKMQYCKHWGVRLPSGVWFEMADKDLFAAARFPECPEGSSIS

APSQTSVDVSLIQDVERILDYSLCQETWSKIRAGLPISPVDLSYLAPKNPGTGPAFTI

INGTLKYFETRYIRVDIAAPILSRMVGMISGTTTERELWDDWAPYEDVEIGPNGVLRT

SSGYKFPLYMIGHGMLDSDLHLSSKAQVFEHPHIQDAASQLPDDESLFFGDTGLSKNP

IELVEGWFSSWKSSIASFFFIIGLIIGLFLVLRVGIHLCIKLKHTKKRQIYTDIEMNR

LGK (SEQ ID NO:3)

FIG. 6D

```
   1 atgaagtgcc ttttgtactt agccttttta ttcattgggg tgaattgcaa gttcaccata
  61 gtttttccac acaaccaaaa aggaaactgg aaaaatgttc cttctaatta ccattattgc
 121 ccgtcaagct cagatttaaa ttggcataat gacttaatag gcacagcctt acaagtcaaa
 181 atgcccaaga gtcacaaggc tattcaagca gacggttgga tgtgtcatgc ttccaaatgg
 241 gtcactactt gtgatttccg ctggtatgga ccgaagtata taacacattc catccgatcc
 301 ttcactccat ctgtagaaca atgcaaggaa agcattgaac aaacgaaaca aggaacttgg
 361 ctgaatccag gcttccctcc tcaaagttgt ggatatgcaa ctgtgacgga tgccgaagca
 421 gtgattgtcc aggtgactcc tcaccatgtg ctggttgatg aatacacagg agaatgggtt
 481 gattcacagt tcatcaacgg aaaatgcagc aattacatat gccccactgt ccataactct
 541 acaacctggc attctgacta taaggtcaaa gggctatgtg attctaacct catttccatg
 601 gacatcacct tcttctcaga ggacggagag ctatcatccc tgggaaagga gggcacaggg
 661 ttcagaagta actactttgc ttatgaaact ggaggcaagg cctgcaaaat gcaatactgc
 721 aagcattggg gagtcagact cccatcaggt gtctggttcg agatggctga taaggatctc
 781 tttgctgcag ccagattccc tgaatgccca gaagggtcaa gtatctctgc tccatctcag
 841 acctcagtgg atgtaagtct aattcaggac gttgagagga tcttggatta ttccctctgc
 901 caagaaacct ggagcaaaat cagagcgggt cttccaatct ctccagtgga tctcagctat
 961 cttgctccta aaaacccagg aaccggtcct gctttcacca taatcaatgg taccctaaaa
1021 tactttgaga ccagatacat cagagtcgat attgctgctc caatcctctc aagaatggtc
1081 ggaatgatca gtggaactac cacagaaagg gaactgtggg atgactggc accatatgaa
1141 gacgtggaaa ttggacccaa tggagttctg aggaccagtt caggatataa gtttcctttta
1201 tacatgattg gacatggtat gttggactcc gatcttcatc ttagctcaaa ggctcaggtg
1261 ttcgaacatc ctcacattca agacgctgct tcgcaacttc ctgatgatga gagtttattt
1321 tttggtgata ctgggctatc caaaaatcca atcgagcttg tagaaggttg gttcagtagt
1381 tggaaaagct ctattgcctc ttttttcttt atcataggt taatcattgg actattcttg
1441 gttctccgag ttggtatcca tcttttgcatt aaattaaagc acaccaagaa aagacagatt
1501 tatacagaca tagagatgaa ccgacttgga aagtga (SEQ ID NO:4)
```

PSEUDOTYPED RETROVIRAL VECTORS AND METHODS OF USE THEREOF

CROSS-REFERENCE

This application claims the benefit of U.S. Provisional Patent Application No. 60/774,141, filed Feb. 15, 2006, which application is incorporated herein by reference in its entirety.

STATEMENT REGARDING FEDERALLY SPONSORED RESEARCH

The U.S. government may have certain rights in this invention, pursuant to grant nos. BES-0094015 awarded by the National Science Foundation.

BACKGROUND

A variety of approaches have been taken to introduce genetic material into cells of an individual. Delivery vehicles, or vectors, based on retroviruses have proven to be effective, both in the laboratory and in the clinic, for introducing genetic material into cells of an individual. Examples of such vectors include murine leukemia virus (MLV) retroviral vectors and lentiviral vectors.

MLV is an enveloped virus with an approximately 8.5 kilobase long, positively stranded RNA genome. The genome encodes two polyproteins that are proteolytically processed to form the eight individual proteins of the virus. The first polyprotein contains seven proteins: the gag region encodes matrix, p12, nucleocapsid, and capsid, which are structural proteins that package two copies of the RNA genome into the capsid. The pol region contains the protease that cleaves the polyprotein into its individual constituents, as well as the reverse transcriptase and integrase proteins important in the viral life cycle. The second polyprotein, encoded by env, is translated from mRNA that is spliced to remove gag-pol. The resulting polyprotein is proteolytically cleaved to form transmembrane (TM) and surface (SU) polypeptides that are linked by disulfide bonds to yield a transmembrane protein spanning the viral surface envelope. In addition to the coding regions, the viral genome contains several regions important for the viral life cycle, including flanking long terminal repeats (LTR) which contain the viral promoter; a region Ψ (psi) important for viral packaging; and several other elements important in viral function.

Delivery vectors based on MLV were first developed by replacing viral genes with a transgene of interest. The retroviral vectors can be deleted of all viral genes, allowing for insertion of a non-MLV gene of interest into the vector, thereby generating recombinant retroviral vectors. The gag and pol genes are supplied on a separate construct for recombinant vector production. Furthermore, env can be replaced with the surface protein of another enveloped virus, such as vesicular stomatitis virus glycoprotein (VSV-G).

Lentiviral vectors are a family of retroviruses that include the human immunodeficiency virus (HIV). Vectors based on HIV have been developed. HIV-based vectors exhibit the natural ability to infect non-dividing cells.

Retroviruses and vectors derived from them require an envelope protein in order to transduce efficiently a target cell. The envelope protein is expressed in the cell producing the virus or vector and becomes incorporated into the virus or vector particles. Use of envelope protein derived from one virus other to package a different virus is known as pseudotyping. As noted above, the endogenous envelope protein of MLV is sometimes replaced with VSV-G, which exhibits greater stability than the MLV envelope protein and can better withstand the conditions of viral purification. In addition, VSV-G allows retroviral vectors to deliver genes to a broad range of target cell types.

There is continued interest in developing pseudotyped retroviral vectors, e.g., pseudotyped recombinant retroviral vectors.

Literature

U.S. Pat. No. 5,817,491; U.S. Pat. No. 5,739,018; U.S. Pat. No. 6,133,027; U.S. Pat. No. 6,432,705; Parrott et al. (2003) *Mol. Ther.* 8:688-700; Schlehuber and Rose (2004) *J. Virol.* 78:5079-5087; Azzouz et al. (2004)*Nature* 429:413-417; Guibing a et al. (2004) *Molec. Therapy* 9:76-84; Wong et al. (2004) *Molec. Therapy* 9:101-111; Li et al. (2003) *J. Virol.* 67:4070-4077.

SUMMARY OF THE INVENTION

The present invention provides nucleic acids encoding recombinant envelope proteins; and packaging cells comprising the nucleic acids, which packaging cells provide for encapsidation of recombinant retroviral vectors. The present invention provides producer cells that produce pseudotyped recombinant retroviral vectors. The present invention further provides methods of purifying pseudotyped recombinant retroviral vectors; and purified pseudotyped recombinant retroviral vectors. The present invention further provides methods of delivering a gene product to an individual. The methods generally involve introducing a subject recombinant retroviral vector into an individual.

BRIEF DESCRIPTION OF THE DRAWINGS

FIGS. 1A-C depict VSV-G-His$_6$ library design. FIG. 1B depicts peptide (SEQ ID NO:34) and DNA (SEQ ID NO:35) sequences for the His$_6$ insert after insertion.

FIGS. 3A and 3B depict VSV-G-His$_6$ library selection.

FIGS. 5A-D depict column purification of VSV-G-His$_6$-pseudotyped retroviral and lentiviral vectors.

FIGS. 6A-D depict VSV-G amino acid and nucleotide sequences.

DEFINITIONS

Figure 2A:
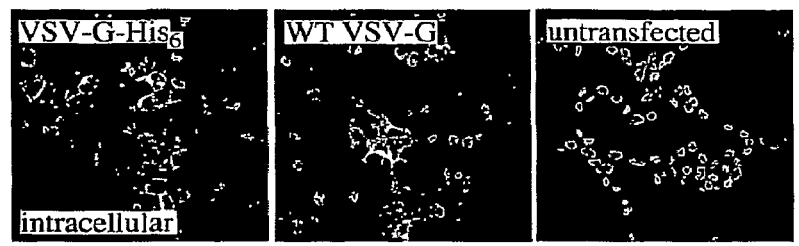
FIGS. 2A-C depict expression of library proteins.

As used herein, the term "viral envelope protein" refers to the protein embedded in the membrane which encapsulates the viral core and which protein is responsible for binding to and entry of the infectious virus into the target cell. The viral envelope protein may also be a fusogenic protein. A "fusogenic protein" refers to glycoproteins which cause viral envelopes to fuse with a target cell membrane or vesicle, or cells within a culture to fuse in multinucleate syncytia. Representative examples of fusogenic proteins include but are not limited to VSV-G and Rabies G protein.

As used herein, the term "viral core" refers to at least the group specific viral structural proteins (Gag) and the viral enzymes (Pol) encoded within a retrovirus genome. These proteins encapsidate the retrovirus-packageable sequences and themselves are further surrounded by a membrane containing an envelope glycoprotein.

As used herein, the term "packaging cell" refers to a cell which contains those elements necessary for production of infectious recombinant virus which are lacking in a recombinant viral vector. Typically, such packaging cells contain one or more expression cassettes which are capable of expressing viral proteins (such as gag, pol and env) but they do not contain a packaging signal.

As used herein, the term "producer cell" or "vector producing cell" refers to a cell which contains all the elements necessary for production of a viral vector such as recombinant viral vectors, recombinant viral vector particles and retroviral delivery systems.

The term "recombinant retroviral vector" (RRV) refers to a vector with sufficient retroviral genetic information to allow packaging of an RNA genome, in the presence of packaging components, into a viral particle capable of infecting a target cell.

The terms "virion," "virus," "viral particle," "viral vector," and "vector particle" are used interchangeably herein to refer to virus and virus-like particles that are capable of introducing a nucleic acid of interest into a cell through a viral-like entry mechanism. Such vector particles can, under certain circumstances, mediate the transfer of heterologous nucleic acids of interest into the cells they infect. By way of example, a retrovirus is capable of reverse transcribing its genetic material into DNA and incorporating this genetic material into a target cell's DNA upon transduction. Such cells are designated herein as "target cells."

The terms "individual," "host," "subject," and "patient" are used interchangeably herein, and refer to a mammal, including, but not limited to, primates, including simians and humans; rodents, including rats and mice; lagomorpha; bovines; equines; ovines; felines; canines; and the like. "Mammal" means a member or members of any mammalian species, and includes, by way of example, canines; felines; equines; bovines; ovines; rodentia, etc. and primates, e.g., humans. Non-human animal models, particularly mammals, e.g. non-human primates, murines, lagomorpha, etc. may be used for experimental investigations.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; (c) relieving the disease, i.e., causing regression of the disease; and (d) relieving the symptoms of the disease (e.g., pain).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given virus, bacterium, organism or cell in nature. As used herein, the term "endogenous nucleic acid" refers to a nucleic acid that is normally found in and/or produced by a given virus, bacterium, organism, or cell in nature. An "endogenous nucleic acid" is also referred to as a "native nucleic acid" or a nucleic acid that is "native" to a given virus, bacterium, organism, or cell.

The term "heterologous nucleic acid," as used herein, refers to a nucleic acid wherein at least one of the following is true: (a) the nucleic acid is foreign ("exogenous") to (i.e., not naturally found in) a given host cell; (b) the nucleic acid comprises a nucleotide sequence that is naturally found in (e.g., is "endogenous to") a given host microorganism or host cell (e.g., the nucleic acid comprises a nucleotide sequence that is endogenous to the host microorganism or host cell) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

"Recombinant," as used herein, means that a particular nucleic acid (DNA or RNA) is the product of various combinations of cloning, restriction, transposition, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences," below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., nucleic acid exogenous to the cell). Genetic change ("modification") can be accomplished either by incorporation of the new nucleic acid into the genome of the host cell (such that the exogenous nucleic acid is genomically integrated), or by transient or stable maintenance of the new nucleic acid as an episomal element. Where the cell is a eukaryotic cell, a permanent genetic change is generally achieved by introduction of the nucleic acid into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo, ex vivo, or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., a subject nucleic acid, a subject vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., a subject nucleic acid, a subject vector, etc. For example, a subject eukaryotic host cell is a genetically modified eukaryotic host cell, by virtue of introduction into a suitable eukaryotic host cell a heterologous nucleic acid, e.g., a subject nucleic acid, a subject vector, etc., that is not normally found in the eukaryotic host cell.

As used herein, the term "metal ion" refers to any metal ion for which the affinity peptide has affinity and that can be used for purification or immobilization of a fusion protein. Such metal ions include, but are not limited to, $Ni^{2+}$, $Co^{2+}$, $Fe^{3+}$, $Al^{3+}$, $Zn^{2+}$ and $Cu^{2+}$. As used herein, the term "hard metal ion" refers to a metal ion that shows a binding preference for oxygen. Hard metal ions include $Fe^{3+}$, $Ca^{2+}$, and $Al^{3+}$. As used herein, the term "soft metal ion" refers to a metal ion that shows a binding preference of sulfur. Soft metal ions include $Cu^+$, $Hg^{2+}$, and $Ag^+$. As used herein, the term "intermediate metal ion" refers to a metal ion that coordinates nitrogen, oxygen, and sulfur. Intermediate metal ions include $Cu^{2+}$, $Ni^{2+}$, $Zn^{2+}$, and $Co^{2+}$.

The terms "adsorbent" and "solid support" are used interchangeably herein, and as used herein refer to a chromatography or immobilization medium used to immobilize a metal ion.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a recombinant retroviral particle" includes a plurality of such particles and reference to "the packaging cell" includes reference to one or more packaging cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides nucleic acids encoding recombinant envelope proteins; and packaging cells comprising the nucleic acids, which packaging cells provide for encapsidation of recombinant retroviral vectors. The present invention provides producer cells that produce pseudotyped recombinant retroviral vectors, as well as pseudotyped retroviral vectors generated by the producer cells. The present invention further provides methods of purifying pseudotyped recombinant retroviral vectors; and purified pseudotyped recombinant retroviral vectors. The present invention provides methods of modifying a recombinant retroviral vector to target delivery of a gene product to a specific target cell. The present invention further provides methods of genetically modifying a host cell; the methods generally involve contacting a target host cell with a subject pseudotyped recombinant viral vector. The present invention further provides methods of delivering a gene product to an individual. The methods generally involve introducing a subject recombinant retroviral vector into an individual.

Recombinant Envelope Nucleic Acids

The present invention provides nucleic acids encoding recombinant envelope proteins ("recombinant envelope nucleic acids"), as well as recombinant envelope proteins encoded by the nucleic acids. A subject variant envelope nucleic acid is useful for generating a packaging cell, as described below, for packing a retroviral vector.

A subject recombinant envelope nucleic acid comprises a nucleotide sequence encoding a recombinant envelope polypeptide. The encoded recombinant envelope polypeptide comprises, in addition to an envelope protein, an insertion of a heterologous polypeptide. The heterologous polypeptide does not substantially adversely affect biological activity of the envelope protein.

A subject recombinant envelope polypeptide is generally of the formula: A-$X_1$—Y—$X_2$—B, where A is an amino-terminal portion of an envelope protein; B is a carboxyl-terminal portion of an envelope protein; Y is a polypeptide heterologous to the envelope protein; and $X_1$ and $X_2$, if present, are linker peptides. In some embodiments, both $X_1$ and $X_2$ are present; in other embodiments, $X_1$ is present and $X_2$ is absent; in other embodiments, $X_1$ is absent and $X_2$ is present; in other embodiments, both $X_1$ and $X_2$ are absent.

The recombinant envelope protein comprises a rhabdovirus envelope protein and a heterologous protein. Suitable rhabdovirus envelope proteins include, but are not limited to a vesicular stomatitis virus glycoprotein (VSV-G); a rabies virus glycoprotein (rabies G protein); a Lyssavirus Mokola virus glycoprotein; an Arenavirus lymphocytic choriomeningitis virus (LCMV); and the like. Suitable rhabdovirus envelope proteins include rhabdovirus envelope proteins with a wild-type amino acid sequence; as well as variants comprising one or more amino acid insertions, and/or substitutions, and/or deletions, as long as the variant envelope protein retains biological activity, e.g., facilitating binding of a packaged retroviral vector to a cell surface, and entry of the packaged retroviral vector into a cell. Variant envelope proteins suitable for inclusion in a subject recombinant envelope protein typically have at least 90% sequence identity with a corresponding wild type amino acid sequence. Variant envelope proteins suitable for inclusion in a subject recombinant envelope protein typically have 20 mutations (e.g., amino acid substitutions) or less over the whole wild-type sequence, e.g., fewer than 20, fewer than 15, fewer than 10, or fewer than 5 mutations the whole wild-type sequence. Also suitable for use are rhabdovirus envelope proteins derived from laboratory passaged strains of rhabdovirus. Exemplary VSV-G amino acid sequences are depicted in FIG. 6A (SEQ ID NO: 1; GenBank Accession Nos. X03633 and CAA27283) and 6C (SEQ ID NO:3; GenBank Accession Nos. AJ318514; and CAC47944). Exemplary rabies G protein amino acid sequences are found in, e.g., GenBank accession number J02293.

Heterologous polypeptides that are suitable for inclusion in a subject recombinant envelope, include, but are not limited to, affinity tags; epitope tags that provide tracking capability; epitope tags that provide for ease of purification; epitope tags that provide for altered antigenicity, e.g., for use in applications involving modulating an immune response; targeting peptides; peptides that promote immunoevasion; peptides that provide for enhanced storage stability; peptides that provide for increased viral transport; and the like.

Heterologous polypeptides can be from about 6 amino acids in length to about 100 amino acids (aa) in length, e.g., from about 6 aa to about 8 aa, from about 8 aa to about 10 aa, from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa.

The heterologous polypeptide is at a position in the envelope protein that does not substantially adversely affect biological activity of the envelope protein. Suitable sites in the envelope protein for inclusion of a heterologous polypeptide include, but are not limited to, between amino acids 16 and 17 of the envelope protein; between amino acids 18 and 19 of the envelope protein; between amino acids 23 and 24 of the envelope protein; and between amino acids 25 and 26 of the envelope protein, e.g., as shown in Table 1, below.

Thus, in some embodiments, a subject recombinant envelope protein is of the formula: A-$X_1$—Y—$X_2$—B, where A is an amino-terminal portion of an envelope protein; B is a carboxyl-terminal portion of an envelope protein; Y is a polypeptide heterologous to the envelope protein. In some embodiments, A is amino acids 1-16 of a rhabdovirus envelope protein (e.g., VSV-G); $X_1$, if present, is a linker; Y is a heterologous protein; $X_2$, if present, is a linker; and B is amino acids 17-511 of a rhabdovirus envelope protein, e.g., VSV-G). In some embodiments, A is amino acids 1-18 of a rhabdovirus envelope protein (e.g., VSV-G); $X_1$, if present, is a linker; Y is a heterologous protein; $X_2$, if present, is a linker; and B is amino acids 19-511 of a rhabdovirus envelope protein, e.g., VSV-G). In some embodiments, A is amino acids 1-23 of a rhabdovirus envelope protein (e.g., VSV-G); $X_1$, if present, is a linker; Y is a heterologous protein; $X_2$, if present, is a linker; and B is amino acids 24-511 of a rhabdovirus envelope protein, e.g., VSV-G). In some embodiments, A is amino acids 1-25 of a rhabdovirus envelope protein (e.g., VSV-G); $X_1$, if present, is a linker; Y is a heterologous protein; $X_2$, if present, is a linker; and B is amino acids 26-511 of a rhabdovirus envelope protein, e.g., VSV-G).

In some embodiments, a linker peptide is included. Suitable linker peptides generally range in length from about 1 amino acid to about 15 amino acids, e.g., from one amino acid to about 3 amino acids, from about 3 amino acids to about 5 amino acids, from about 5 amino acids to about 7 amino acids, from about 7 amino acids to about 10 amino acids, from about 10 amino acids to about 12 amino acids, or from about 12 amino acids to about 15 amino acids.

Generally, any flexible linker is suitable for use. Exemplary linkers for use in a subject recombinant envelope protein generally include a combination of one or more of glycine, serine, alanine, proline, and methionine residues. Suitable linkers comprise amino acids sequences including, but not limited to, GGS; SSGS (SEQ ID NO:5); SGG; GGSGGS (SEQ ID NO:6); AAAGGM (SEQ ID NO:7); AAAGGMP-PAAAGGM (SEQ ID NO:8); AAAGGM (SEQ ID NO:9); and PPAAAGGM (SEQ ID NO:10). Linkers may have virtually any sequence that results in a generally flexible peptide, including sequences of the type exemplified above. Additionally, the entire peptide insert (including linkers) may be flanked by cysteine residues to create a loop structure, closed by a disulfide bond.

Epitope Tags

Suitable epitope tags include epitope that provide tracking capability; epitope tags that provide for ease of purification; epitope tags that provide for altered antigenicity, e.g., for use in applications involving modulating an immune response. Epitope tags that provide tracking capability ("tracking epitopes") include any epitope capable of being specifically bound by an antibody, e.g., a detectably labeled antibody, such that the tracking epitope is accessible, on the surface of a pseudotyped viral particle containing the tracking epitope, to antibody. Detectably labeled antibodies include antibody comprising one or more different detectable labels attached to the antibody, where suitable detectable labels include directly detectable labels such as fluorescent proteins, radioisotopes, and the like, which on their own generate a detectable signal; labels that modify a substrate and generate a detectable product, e.g., luciferase, horse radish peroxidase, alkaline phosphatase, and the like; and indirectly detectable labels, e.g., first members of a specific binding pair which are detected using a detectably labeled second member of a specific binding pair, where specific binding pairs include, e.g., biotin/avidin, and the like.

Metal Ion Affinity Peptides

Suitable affinity tags ("affinity peptides") include, but are not limited to, peptides that provide for binding to a metal ion. Metal ion affinity peptides are known in the art, and any known metal ion binding peptide can be used in a subject recombinant envelope protein. See, e.g., Itakura, et al., *Science* 198:1056-63 (1977); Germino, et al., *Proc. Natl. Acad. Sci. USA* 80:6848-52 (1983); Nilsson et al., *Nucleic Acids Res.* 13:1151-62 (1985); Smith et al., *Gene* 32:321-27 (1984); Dobeli, et al., U.S. Pat. No. 5,284,933; Dobeli, et al., U.S. Pat. No. 5,310,663; U.S. Pat. No. 4,569,794; U.S. Pat. No. 5,594,115; and U.S. Patent Publication No. 2002/0164718.

Metal ion affinity peptides typically bind to intermediate metal ions with an affinity of from about $10^{-3}$ M$^{-1}$ to about $10^{-9}$ M$^{-1}$; and to hard metal ions with an affinity of from about $10^{-3}$ M$^{-1}$ to about $10^{-9}$ M$^{-1}$. Metal ion affinity peptides typically contain from about 30% to about 50%, from about 33% to about 45%, from about 35% to about 43%, or from about 37% to about 40%, histidine residues. For example, a metal ion affinity peptide 18 amino acids in length may contain 6, 7, or 8 histidine residues. Metal ion affinity peptides are generally from about 6 to about 30, from about 7 to about 25, from about 8 to about 20, from about 9 to about 18, from about 10 to about 16, or from about 12 to about 14 amino acids in length.

In some embodiments, a metal ion affinity peptide comprises the amino acid sequence (His)$_n$, where n=3-18, e.g., where n=3-6, 6-8, 8-10, or 10-18. In some embodiments, n=6. In other embodiments, the metal ion affinity peptide comprises an amino acid sequence as set forth in U.S. Patent Publication No. 2002/0164718. In some embodiments, a metal ion affinity peptide comprises a peptide of the formula: (His-($X_1$)$_n$)$_m$, wherein m≧3, wherein $X_1$ is any amino acid other than His, wherein n=1-3, provided that, in at least one His-($X_1$)$_n$ unit, n>1.

In some embodiments, a metal ion affinity peptide comprises a peptide of the formula: (His-$X_1$-$X_2$)$_{n1}$-(His-$X_3$-$X_4$-$X_5$)$_{n2}$-(His-$X_6$)$_{n3}$, wherein each of $X_1$ and $X_2$ is independently an amino acid with an aliphatic or an amide side chain, each of $X_3$, $X_4$, $X_5$ is independently an amino acid with a basic side chain (except His) or an acidic side chain, each $X_6$ is an amino acid with an aliphatic or an amide side chain, n1 and n2 are each independently 1-3, and n3 is 1-5.

In some embodiments, each of $X_1$ and $X_2$ is independently selected from Leu, Ile, Val, Ala, Gly, Asn, and Gln. In other embodiments, each of $X_1$ and $X_2$ is independently selected from Leu, Val, Asn, and Ile. In some embodiments, each of $X_3$, $X_4$, $X_5$ is independently selected from Lys, Arg, Asp, and Glu. In some embodiments, each of $X_3$, $X_4$, $X_5$ is independently selected from Lys and Glu. In some embodiments, each $X_6$ is independently selected from Leu, Ile, Val, Ala, Gly, Asn, and Gln. In other embodiments, each $X_6$ is independently selected from Ala and Asn. In one particular embodiment, the affinity peptide has the amino acid sequence NH$_2$-His-Leu-Ile-His-Asn-Val-His-Lys-Glu-Glu-His-Ala-His-Ala-His-Asn-COOH (SEQ ID NO:11).

In some embodiments, a metal ion affinity peptide has the formula (His-Asn)$_n$, wherein n=3 to 10. In certain embodiments, n=from about 4 to about 10, and preferably from about 5 to about 10. In one particular embodiment, n=6.

In some embodiments, a metal ion affinity peptide has the formula (His-$X_1$-$X_2$)$_n$, wherein each of $X_1$ and $X_2$ is an amino acid having an acidic side chain, and n=3 to 10. In one embodiment, the affinity peptide comprises the sequence (His-Asp-Asp)$_6$. In another embodiment, the affinity peptide comprises the sequence (His-Glu-Glu)$_6$. In a further embodiment, the affinity peptide comprises the sequence (His-Asp-Glu)$_6$. In a further embodiment, the affinity peptide comprises the sequence (His-Glu-ASP)$_6$.

Targeting Peptides

In some embodiments, the heterologous polypeptide is one that provides for targeting of a virion that comprises a subject recombinant envelope protein to a cell, e.g., a cell type, a tissue type, etc. A targeting peptide mediates selective localization of the pseudotyped viral particle to a particular cell, a particular cell type, a particular tissue, or a cell in a particular state (e.g., a cancerous state). In some embodiments, the targeting peptide provides for targeting to hematopoietic stem cells. In other embodiments, the targeting peptide provides for targeting to tumor cells. In other embodiments, the targeting peptide provides for targeting to endothelial cells. Endothelial cell targeting peptides are described in, e.g., Müller et al. ((2003) *Nature Biotechnol.* 21:1040-1046). Suitable targeting peptides include, but are not limited to, a) endothelial targeting peptides including, but not limited to, SIGYPLP (SEQ ID NO:12); an $\alpha_v$ integrin binding peptide; an RGD-containing peptide, e.g., ($X_1$)$_n$-RGD-($X_2$)$_m$, where $X_1$ and $X_2$ are any amino acid, and n and m are independently 0-20; an integrin-binding peptide as described in U.S. Patent Publication No. 2002/0103130; an integrin-binding peptide as described in U.S. Patent Publication No. 2003/0143733; a growth factor, or a growth factor receptor-binding fragment thereof; a cytokine, or a cytokine receptor-binding fragment thereof; an epidermal growth factor (EGF) or an EGF receptor-binding fragment thereof, targeting cells that express an EGF receptor (see, e.g., GenBank Accession No. AAS83395 for an amino acid sequence of an EGF); a stromal-derived factor-1α or a CXCR4-binding fragment thereof, targeting cells expressing CXCR4 (see, e.g., GenBank Accession No. NP-954637 for an amino acid sequence of an SDF-1α); a collagen-binding domain, e.g., GHAWREPGRMELNGAA (SEQ ID NO:13); a peptide comprising one of: GGGVFWQ (SEQ ID NO:14), HGRVRPH (SEQ ID NO:15), VVLVTSS (SEQ ID NO:16), CLHRGNSC (SEQ ID NO:17), CRSWNKADNRSC (SEQ ID NO:18), for targeting to heart cells (see, e.g., U.S. Patent Publication No. 2003/0045476; a tumor-targeting peptide, e.g., NGRAHA (SEQ ID NO:19), CDCRGDCFC (SEQ ID NO:20), CNGRC (SEQ ID NO:21), CNGRCVSGCAGRC (SEQ ID NO:22), or CGSLVRC (SEQ ID NO:23); a peptide that provides for targeting to breast tissue, e.g., PGPEGAG (SEQ ID NO:24), or CPGPEGAGC (SEQ ID NO:25); a targeting peptide as described in U.S. Patent Publication No. 2004/0071689; a peptide that provides for targeting to tumor lymphatic vasculature, e.g., GNKRTRG (SEQ ID NO:26), CGNKRTRGC (SEQ ID NO:27); a peptide that targets the angiogenic vasculature of a tumor, e.g., a nerve growth factor receptor-binding peptide, e.g., CNGRCVSGCAGRC (SEQ ID NO:22), NGRAHA (SEQ ID NO:19), CVLNGRMEC (SEQ ID NO:28), and CNGRC (SEQ ID NO:21); a peptide that targets the fibroblast growth factor receptor, e.g., GRGVVSI(F)KGV (SEQ ID NO:29; see, e.g., Ray et al. (1997) *PNAS* 94:7047); a peptide that targets heparan sulfate or heparin, e.g. FHRRIKA (SEQ ID NO:30) (see, e.g., Harbers et al., *J. Biomat. Res.* 75:855, 2005); a peptide that targets a serpin receptor, e.g. KFNK-PFVFLI (SEQ ID NO:31; see, e.g., Wu et al., *J Virology* 74:8635, 2000); etc.

Control Elements

In some embodiments, a subject recombinant envelope nucleic acid comprises a nucleotide sequence encoding a recombinant envelope protein, as described above, where the recombinant envelope-encoding nucleotide sequence is operably linked to a control element, e.g., a promoter. A subject recombinant envelope nucleic acid may also contain a ribosome binding site for translation initiation; and a transcription terminator.

Suitable promoters include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), apagC promoter (Pulkkinen and Miller, *J. Bacteriol.*, 1991: 173(1): 86-93; Alpuche-Aranda et al., PNAS, 1992; 89(21): 10079-83), a nirB promoter (Harbome et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). Mol. Microbiol. 22:367-378); a tet promoter (see, e.g., Hillen; W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035-7056); and the like.

In some embodiments, promoters suitable for use include those that are functional in a eukaryotic cell. Suitable promoters include CMV immediate early, HSV thymidine kinase, early and late SV40, LTRs from retrovirus, human ubiquitin C promoter, and mouse metallothionein-I. In some embodiments, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, and the like. Selection of the appropriate vector and promoter is well within the level of ordinary skill in the art.

Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) *J. Bacteriol.* 177:4121-4130); a xylose-inducible promoter, e.g., Pxyl (see, e.g., Kim et al. (1996) *Gene* 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) *FEMS Microbiol Lett.* 177(2):327-34); and the like.

In some embodiments, the promoter is an inducible promoter. In some embodiments, the inducible promoter is a tetracycline-inducible promoter. In some embodiments, the promoter is an inducible system such as described in U.S. Pat. No. 6,969,598.

Recombinant Vectors

The present invention further provides recombinant vectors, including expression vectors ("expression constructs"), comprising a subject recombinant envelope nucleic acid. Numerous suitable expression vectors are known to those of skill in the art, and many are commercially available. The following vectors are provided by way of example: pBluescript (Stratagene, San Diego, Calif.), pQE vectors (Qiagen), pBluescript plasmids, pNH vectors, lambda-ZAP vectors (Stratagene); pTrc (Amann et al., Gene, 69:301-315 (1988)); pTrc99a, pKK223-3, pDR540, and pRIT2T (Pharmacia); for eukaryotic host cells: pXT1, pSGs (Stratagene), pSVK3, pBPV, pMSG, and pSVLSV40 (Pharmacia). Numerous retroviral vectors are known to those of skill in the art, and many are commercially available. The following vectors are provided by way of example: pLXSN, pLNCX2, pQCXIN, pQCXIX retroviral vectors (Clontech), pFB, pFBNeo retroviral vectors (Stratagene), RTV vectors (Cell Biolabs), pLenti vectors (Invitrogen), pFIV vectors (System Biosciences).

A subject recombinant vector will in many embodiments contain one or more selectable marker genes to provide a phenotypic trait for selection of transformed host cells. Suitable selectable markers include, but are not limited to, dihydrofolate reductase, neomycin resistance for eukaryotic cell culture; and tetracycline or ampicillin resistance in prokaryotic host cells such as E. coli.

Generally, recombinant expression vectors will include origins of replication and selectable markers permitting transformation of the host cell, e.g., the ampicillin resistance gene of E. coli, the S. cerevisiae TRP1 gene, etc.; and a promoter derived from a highly-expressed gene to direct transcription of the coding sequence. Such promoters can be derived from operons encoding glycolytic enzymes such as 3-phosphoglycerate kinase (PGK), α-factor, acid phosphatase, or heat shock proteins, among others.

Compositions

The present invention further provides compositions comprising a subject nucleic acid. The present invention further provides compositions comprising a subject recombinant vector. Compositions comprising a subject nucleic acid; or a subject recombinant vector, e.g., a subject expression vector will in many embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like. In some embodiments, a subject nucleic acid or a subject recombinant vector is lyophilized.

Packaging Cells

The present invention provides packaging cells comprising subject nucleic acids, which packaging cells provide for encapsidation of recombinant retroviral vectors. Thus, in some embodiments, a subject packaging cell comprises: a) a first nucleic acid comprising a nucleotide sequence encoding a recombinant envelope protein, as described above; and b) a second nucleic acid comprising a nucleotide sequence encoding retroviral core proteins.

Packaging cell lines may be readily prepared (see e.g., WO 92/05266), and utilized to create producer cell lines for the production of retroviral vector particles.

The packaging cell lines provide the gene products necessary to encapsidate the recombinant retroviral vector; and provide a membrane protein for retroviral vector particle production. The packaging cell may be a cell cultured in vitro such as a tissue culture cell line. Suitable cell lines include, but are not limited to, mammalian cells such as murine fibroblast derived cell lines (e.g., NIH 3T3 cells (e.g., ATCC CRL1658)); or human cell lines. In some embodiments, the packaging cell line is a human cell line, such as for example: HEK 293 cells (e.g., ATCC CRL-1573); HEK 293T cells; a human medulloblastoma cell line, e.g., TE671 cells (e.g., ATCC CRL8805); Phoenix (e.g. ATCC SD 3444); a human fibrosarcoma cell line, e.g., HT1080 cells (e.g., ATCC CCL-121); CHO cells (e.g., ATCC CCL-61); a human ovarian carcinoma cell line, e.g., HeLa cells (e.g., ATCC CCL-2); BOSC23 (e.g., ATCC CRL-11270); and the like. Derivatives of such cell lines are also suitable for use. Many such cells are available from the American Type Culture Collection (ATCC). Other suitable packaging cells are described in, e.g., U.S. Pat. Nos. 6,958,226, and 6,818,209.

In some embodiments, the packaging cell comprises a provirus in which the packaging signal has been deleted. In other embodiments, the packaging cell line is a so-called "second generation cell line," wherein the 3' LTR of the provirus is deleted. In other embodiments, the packaging cell line is a so-called "third generation cell line," in which the gag-pol genes and the env gene are on separate constructs so-called third generation packaging cell lines. In some embodiments, the codons of one or more of the viral genes have been altered so as to reduce homology between the separate constructs, for example between the regions of overlap in the gag-pol and env open reading frames (ORFs), thereby reducing the likelihood of homologous recombination between viral ORFs. In some embodiments, at least the gag and pol sequences are codon optimized. See, e.g., U.S. Pat. No. 6,958,226 for codon optimized gag and pol sequences.

Alternatively, in some embodiments, the packaging cell is a cell derived from the individual to be treated such as a monocyte, macrophage, blood cell or fibroblast. The cell may be isolated from an individual and the packaging and vector components administered ex vivo followed by re-administration of the autologous packaging cells.

A subject packaging cell line provides the gene products necessary to encapsidate a recombinant retroviral vector; and provides a membrane protein for a viral vehicle such as a retrovirus and retrovirus nucleic gene delivery vehicle. As described below, when viral sequences such as retrovirus sequences are introduced into a subject packaging cell line, such sequences are encapsidated with the viral core proteins and these units then bud through the cell membrane to become surrounded in cell membrane and to contain the envelope protein produced in the packaging cell line. These infectious retroviruses are useful as infectious units per se or as delivery vectors.

Producer Cells

The present invention provides producer cells that produce pseudotyped recombinant retroviral vectors. A subject producer cell comprises: a) a first nucleic acid comprising a nucleotide sequence encoding a recombinant envelope protein, as described above; b) a second nucleic acid comprising a nucleotide sequence encoding the retroviral core proteins; and c) a third nucleic acid comprising a retroviral sequence capable of being encapsidated in the viral core. In many embodiments, the third nucleic acid is a retroviral construct comprising a retroviral LTR; a packaging signal (Ψ, or psi, region); and a heterologous nucleic acid of interest, where the heterologous nucleic acid of interest comprises, operably linked to one or more control elements, a nucleotide sequence encoding a gene product.

A subject producer cell is useful for the production of infectious pseudotyped retrovirus, and vector particles, e.g., virions may also contain one or more nucleic acids of interest capable of being expressed in a host target cell or tissue. The cells are thus useful for packaging a viral vector genome such as a retrovirus genome which may also contain a heterologous nucleic acid of interest capable of being expressed in a target cell or tissue.

As used herein, the term "long terminal repeat" (LTR) is used in reference to domains of base pairs located at the end of retroviral DNAs. In some embodiments, the retroviral vector is a regulated retroviral vector. As used herein, the term "regulated retroviral vectors" refers to a retroviral vector comprising a "regulatable 3'LTR region. As used herein, the terms "regulatable LTR" and "regulatable 3' LTR" include vectors which contain responsive elements which are present in retroviral 3' LTR sequences, either by design or by their nature. Within the regulatable 3'LTR region, the 3'U3 sequence contains most of the transcriptional control elements of the provirus, which include the promoter and multiple enhancer sequences responsive to cellular and in some cases, viral transcriptional activator proteins.

As used herein, the term "packaging signal" which is referred to interchangeably as "packaging sequence" or "psi" is used in reference to the non-coding sequence located within the retroviral genome which is required for encapsidation of retroviral RNA strands during viral particle formation. In HIV-1, this sequence has been mapped to loci extending from upstream of the major splice donor site (SD) to at least the gag start codon. Several retroviral vectors use the minimal packaging signal (also referred to as the psi sequence) needed for encapsidation of the viral genome. By way of example, this minimal packaging signal encompasses bases 212 to 563 of the Mo-MLV genome (Mann et al 1983: Cell 33:153).

As used herein, the term "extended packaging signal" or "extended packaging sequence" refers to the use of sequences around the psi sequence with further extension into the gag gene. The inclusion of these additional packaging sequences may increase the efficiency of insertion of vector RNA into viral particles.

Heterologous nucleic acids of interest are described below.

Viral Particles Comprising a Recombinant Envelope Protein

The present invention provides viral particles comprising a recombinant envelope protein, as described above. In some embodiments, the viral particles are pseudotyped retroviral particles, as described below. In other embodiments, the viral particles comprise a recombinant envelope protein, as described above, and a recombinant VSV vector (rVSV) packaged within the particle. In some embodiments, the rVSV vector comprises a heterologous nucleic acid comprising a nucleotide sequence encoding an antigen. Viral particles comprising an rVSV comprising a nucleotide sequence encoding an antigen are useful to stimulate an immune response to the antigen in a mammalian host. The present invention provides immunogenic compositions comprising a subject viral particle comprising an rVSV, where the rVSV comprises a nucleotide sequence encoding an antigen.

Pseudotyped Retroviral Vectors

The present invention provides pseudotyped retroviral vectors. A subject pseudotyped recombinant retroviral vector includes a heterologous nucleic acid of interest (where "heterologous nucleic acid of interest" is also referred to herein as "heterologous nucleic acid" or "nucleic acid of interest"). A subject pseudotyped recombinant retroviral vector is useful for delivering a gene product into a host cell (e.g., a "target cell" or a "target host cell").

A subject pseudotyped recombinant retroviral vector comprises a recombinant retroviral construct comprising a nucleic acid of interest and operatively linked components in the direction of transcription. Thus, e.g., the recombinant retroviral construct comprises control elements including a transcriptional initiation region, a nucleic acid of interest, and a transcriptional termination region. The control elements are typically selected to be functional in a eukaryotic host cell. The resulting construct which contains the operatively linked components is bounded (5' and 3') with functional retroviral LTR sequences. The construct further comprises a Ψ site.

Retroviruses include, but are not limited to, murine leukemia virus (MLV), human immunodeficiency virus (HIV), equine infectious anaemia virus (EIAV), feline immunodeficiency virus (FIV), simian immunodeficiency virus (SIV), human T cell leukemia virus (HTLV), mouse mammary tumor virus (MMTV), Rous sarcoma virus (RSV), avian sarcoma virus (ASV), Fujinami sarcoma virus (FuSV), Moloney murine leukemia virus (Mo-MLV), FBR murine osteosarcoma virus (FBR MSV), Moloney murine sarcoma virus (Mo-MSV), spleen necrosis virus (SNV), reticuloendotheliosis virus A (REV-A), Abelson murine leukemia virus (A-MLV), Friend murine leukemia virus (FMLV), Avian myelocytomatosis virus-29 (MC29), Avian erythroblastosis virus (AEV), and the family of spumaviruses, such as human foamy virus (HFV) and simian foamy virus (SFV). Retroviral vectors and lentiviral vectors are also described in U.S. Pat. Nos. 6,669,936 and 6,531,123.

Lentiviruses can be divided into primate and non-primate groups. Examples of primate lentiviruses include but are not limited to: the human immunodeficiency virus (HIV), the causative agent of human auto-immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

In some embodiments, the viral vector, is a self-inactivating vector. Self-inactivating retroviral vectors have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus (Yu et al 1986 Proc Natl Acad Sci 83: 3194-3198; Dougherty and Temin 1987 Proc Natl Acad Sci 84: 1197-1201; Hawley et al 1987 Proc Natl Acad Sci 84: 2406-2410; Yee et al 1987 Proc Natl Acad Sci 91: 9564-9568). However, any promoter(s) internal to the LTRs in such vectors will still be transcriptionally active. This strategy has been employed to eliminate effects of the enhancers and promoters in the viral LTRs on transcription from internally placed genes. Such effects include increased transcription (Jolly et al 1983 Nucleic Acids Res 11: 1855-1872) or suppression of transcription (Emerman and Temin 1984 Cell 39: 449-467). This strategy can also be used to eliminate downstream transcription from the 3' LTR into genomic DNA (Herman and Coffin 1987 Science 236: 845-848).

Heterologous Nucleic Acids

A suitable heterologous nucleic acid (also referred to herein as a "heterologous nucleic acid" or "nucleic acid of interest") for use in a subject recombinant retroviral vector will generally be less than about 10 kilobases (kb) in size (e.g., less than about 10 kb, less than about 9 kb, less than about 8 kb, less than about 7 kb, less than about 6 kb, less than about 5 kb) and will include, for example, a gene (a nucleotide sequence) that encodes a protein that is defective or missing from a recipient subject; a gene that encodes a protein having a desired biological or therapeutic effect (e.g., an antibacterial, antiviral or antitumor function); a nucleotide sequence that encodes an RNA that inhibits or reduces production of a deleterious or otherwise undesired protein; a nucleotide sequence that encodes an antigenic protein; or a nucleotide sequence that encodes an RNA that inhibits or reduces production of a protein.

Suitable heterologous nucleic acids include, but are not limited to, those encoding proteins used for the treatment of endocrine, metabolic, hematologic, cardiovascular, neurologic, musculoskeletal, urologic, pulmonary and immune disorders, including such disorders as inflammatory diseases, autoimmune, chronic and infectious diseases, such as acquired immunodeficiency syndrome (AIDS), cancer, hypercholestemia, insulin disorders such as diabetes, growth disorders, various blood disorders including various anemias, thalassemias and hemophilia; genetic defects such as cystic fibrosis, Gaucher's Disease, Hurler's Disease, adenosine deaminase (ADA) deficiency, emphysema, or the like.

Suitable heterologous nucleic acids include, but are not limited to, those encoding any of a variety of proteins, including, but not limited to: an interferon (e.g., IFN-γ, IFN-α, IFN-β, IFN-ω; IFN-τ); an insulin (e.g., Novolin, Humulin, Humalog, Lantus, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β; and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); and the like), including an antigen-binding fragment of a monoclonal antibody; a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as Enbrel® (etanercept); a soluble VEGF receptor; a soluble interleukin receptor; a soluble γ/δ T cell receptor; and the like); an enzyme (e.g., α-glucosidase; Cerazyme® (imiglucarase; β-glucocerebrosidase, Ceredase® (alglucerase); an enzyme activator (e.g., tissue plasminogen activator); a chemokine (e.g., IP-10; Mig; Groα/IL-8, RANTES; MIP-1α; MIP-1β; MCP-1; PF-4; and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like. Suitable nucleic acids also include those that encode a functional fragment of any of the aforementioned proteins; and nucleic acids that encode functional variants of any of the aforementioned proteins.

Suitable heterologous nucleic acids also include those that encode antigenic proteins. A subject recombinant retroviral vector that comprises a heterologous nucleic acid that encodes an antigenic protein is suitable for stimulating an immune response to the antigenic protein in a mammalian host. The antigenic protein is derived from an autoantigen, an allergen, a tumor-associated antigen, a pathogenic virus, a pathogenic bacterium, a pathogenic protozoan, a pathogenic helminth, or any other pathogenic organism that infects a mammalian host. As used herein, the term "a nucleic acid encoding an antigenic protein derived from" includes nucleic acids encoding wild-type antigenic proteins, e.g., a nucleic acid isolated from a pathogenic virus that encodes a viral protein; synthetic nucleic acids generated in the laboratory that encode antigenic proteins that are identical in amino acid sequence to a naturally-occurring antigenic protein; synthetic nucleic acids generated in the laboratory that encode antigenic proteins that differ in amino acid sequence (e.g., by from one amino acid to about 15 amino acids) from a naturally-occurring antigenic protein, but that nonetheless induce an immune response to the corresponding naturally-occurring antigenic protein; synthetic nucleic acids generated in the laboratory that encode fragments of antigenic proteins (e.g., fragments of from about 5 amino acids to about 50 amino acids, which fragments comprises one or more antigenic epitopes), which fragments induce an immune response to the corresponding naturally-occurring antigenic protein; etc.

Similarly, an antigenic protein "derived from" an autoantigen, an allergen, a tumor-associated antigen, a pathogenic virus, a pathogenic bacterium, a pathogenic protozoan, a pathogenic helminth, or any other pathogenic organism that infects a mammalian host, includes proteins that are identical in amino acid sequence to a naturally-occurring antigenic protein, and proteins that differ in amino acid sequence (e.g., by from one amino acid to about 15 amino acids) from a naturally-occurring antigenic protein, but that nonetheless induce an immune response to the corresponding naturally-occurring antigenic protein; and fragments of antigenic proteins (e.g., fragments of from about 5 amino acids to about 50 amino acids, which fragments comprises one or more antigenic epitopes), which fragments induce an immune response to the corresponding naturally-occurring antigenic protein.

In some embodiments, an immune response to an antigenic protein encoded by a subject recombinant retroviral vector will stimulate a protective immune response to a pathogenic organism that displays the antigenic protein or antigenic epitope (or a protein or an epitope that is cross-reactive with the subject recombinant retroviral vector-encoded antigenic protein or antigenic epitopes) in the mammalian host. In some embodiments, a cytotoxic T lymphocyte (CTL) response to the subject recombinant retroviral vector-encoded antigenic protein will be induced in the mammalian host. In other embodiments, a humoral response to the subject recombinant retroviral vector-encoded antigenic protein will be induced in the mammalian host, such that antibodies specific to the antigenic protein are generated. In many embodiments, a TH1 immune response to the subject recombinant retroviral vector-encoded antigenic protein will be induced in the mammalian host. Suitable antigenic proteins include tumor-associated antigens, viral antigens, bacterial antigens, and protozoal antigens; and antigenic fragments thereof. In some embodiments, the antigenic protein is derived from an intracellular pathogen. In other embodiments, the antigenic protein is a self-antigen. In yet other embodiments, the antigenic protein is an allergen.

Tumor-specific antigens include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M112154). Other tumor-specific antigens include the Ras peptide and p53 peptide associated with advanced cancers, the HPV 16/18 and E6/E7 antigens associated with cervical cancers, MUCI1-KLH antigen associated with breast carcinoma (e.g., GenBank Accession No. J03651), CEA (carcinoembryonic antigen) associated with colorectal cancer (e.g., GenBank Accession No. X9811), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Thus, the present invention can be used as immunotherapeutics for cancers including, but not limited to, cervical, breast, colorectal, prostate, lung cancers, and for melanomas.

Viral antigens are derived from known causative agents responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and human immunodeficiency virus (e.g., GenBank Accession No. U18552).

Suitable bacterial and parasitic antigens include those derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

Suitable heterologous nucleic acids that encode heterologous gene products include non-translated RNAs, such as an antisense RNA, a ribozyme, an RNAi and an siRNA. Interfering RNA (RNAi) fragments, particularly double-stranded (ds) RNAi, can be used to inhibit gene expression. One approach well known in the art for inhibiting gene expression is short interfering RNA (siRNA) mediated gene silencing, where the level of expression product of a target gene is reduced by specific double stranded siRNA nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WOO/44895, WO99/32619, WO01/75164, WO01/92513, WO01/29058, WO01/89304, WO02/16620, and WO02/29858; and U.S. Patent Publication No. 20040023390 for descriptions of siRNA technology. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

Target genes include any gene encoding a target gene product (RNA or protein) that is deleterious (e.g., pathological); a target gene product that is malfunctioning; a target gene product. Target gene products include, but are not limited to, huntingtin; hepatitis C virus; human immunodeficiency virus; amyloid precursor protein; tau; a protein that includes a polyglutamine repeat; a herpes virus (e.g., varicella zoster); any pathological virus; and the like.

As such a subject recombinant retroviral vector that includes a heterologous nucleic acid encoding an siRNA is useful for treating a variety of disorders and conditions, including, but not limited to, neurodegenerative diseases, e.g., a trinucleotide-repeat disease, such as a disease associated with polyglutamine repeats, e.g., Huntington's disease, spinocerebellar ataxia, spinal and bulbar muscular atrophy (SBMA), dentatorubropallidoluysian atrophy (DRPLA), etc.; an acquired pathology (e.g., a disease or syndrome manifested by an abnormal physiological, biochemical, cellular, structural, or molecular biological state) such as a viral infection, e.g., hepatitis that occurs or may occur as a result of an HCV infection, acquired immunodeficiency syndrome, which occurs as a result of an HIV infection; and the like.

In some embodiments, an siRNA is directed against a member of a signal transduction pathway, e.g., the insulin pathway, including AKT1-3, CBL, CBLB, EIF4EBP1, FOXO1A, FOXO3A, FRAP1, GSK3A, GSK3B, IGF1, IGF1R, INPP5D, INSR, IRS1, MLLT7, PDPK1, PIK3CA, PIK3CB, PIK3R1, PIK3R2, PPP2R2B, PTEN, RPS6, RPS6KAI, RPX6KA3, SGK, TSC1, TSC2, and XPO1); an apoptotic pathway (CASP3,6,7,8,9, DSH1/2, P110, P85, PDK1/2, CATENIN, HSP90, CDC37, P23, BAD, BCLXL, BCL2, SMAC, and others); and pathways involved in DNA damage, cell cycle, and the like (p53, MDM2, CHK1/2, BRCA1/2, ATM, ATR, P1151NK4, P27, P21, SKP2, CDC25C/A, 14-3-3, PLK, RB, CDK4, GLUT4, Inos, Mtor, FKBP, PPAR, RXR, ER). Similarly, genes involved in immune system function including TNFR1, IL-IR, IRAK1/2, TRAF2, TRAF6, TRADD, FADD, IKKε, IKKγ, IKKβ, IKKα, IkBα, IkBβ, p50, p65, Rac, RhoA, Cdc42, ROCK, Pak1/2/3/4/5/6, cIAP, HDAC1/2, CBP, β-TrCP, Rip2/4, and others are also important targets for siRNAs, where such siRNAs can be useful in treating immune system disorders. siRNAs specific for gene products involved in apoptosis, such as Dsh1/2, PTEN, P110 (pan), P85, PDK1/2, Akt1, Akt2, Akt (pan), $p70^{S6K}$, GSK3β, PP2A (cat), β-catenin, HSP90, Cdc37/p50, P23, Bad, BclxL, Bcl2, Smac/Diablo, and Ask1 are useful in the treatment of diseases that involve defects in programmed cell death (e.g. in the treatment of cancer). siRNA agents directed against p53, MDM2, Chk1/2, BRCA1/2, ATM, ATR, $p15^{INK4}$, P27, P21, Skp2, Cdc25C/A, 14-3-3sigma/ε, PLK, Rb, Cdk4, Glut4, iNOS, mTOR, FKBP, PPARγ, RXRα, ERα, and related genes can be used to treat diseases associated with disruptions in DNA repair, and cell cycle abnormalities, where such diseases include cancer. Examples of such siRNAs and targets are known in the art; see, e.g., US Patent Publication No. 2005/0246794.

As such a subject recombinant retroviral vector that includes a heterologous nucleic acid encoding an siRNA is useful for treating disorders resulting from or associated with dysregulated cell cycle, e.g., cancer.

In many embodiments, a heterologous nucleic acid encoding an siRNA is operably linked to a promoter. Suitable promoters are known those skilled in the art and include the promoter of any protein-encoding gene, e.g., an endogenously regulated gene or a constitutively expressed gene. For example, the promoters of genes regulated by cellular physiological events, e.g., heat shock, oxygen levels and/or carbon monoxide levels, e.g., in hypoxia, may be operably linked to an siRNA-encoding nucleic acid.

The selected heterologous nucleotide sequence, such as EPO-encoding or nucleic acid of interest, is operably linked to control elements that direct the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, such as the human ubiquitin C promoter, a cytomegalovirus (CMV) promoter such as the CMV immediate early promoter region (CMVIE), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In some embodiments, cell type-specific or tissue-specific promoter will be operably linked to the heterologous nucleic acid encoding the heterologous gene product, such that the gene product is produced selectively or preferentially in a particular cell type(s) or tissue(s). In some embodiments, an inducible promoter will be operably linked to the heterologous nucleic acid.

For example, muscle-specific and inducible promoters, enhancers and the like, are useful for delivery of a gene product to a muscle cell. Such control elements include, but are not limited to, those derived from the actin and myosin gene families, such as from the myoD gene family; the myocyte-specific enhancer binding factor MEF-2; control elements derived from the human skeletal actin gene and the cardiac actin gene; muscle creatine kinase sequence elements and the murine creatine kinase enhancer (mCK) element; control elements derived from the skeletal fast-twitch troponin C gene, the slow-twitch cardiac troponin C gene and the slow-twitch troponin I gene; hypoxia-inducible nuclear factors; steroid-inducible elements and promoters, such as the glucocorticoid response element (GRE); the fusion consensus element for RU486 induction; and elements that provide for tetracycline regulated gene expression.

Methods of Producing a Pseudotyped Retroviral Vector

The present invention provides a method of producing a pseudotyped retroviral vector, as described above, the method generally involving culturing a subject producer cell in a suitable culture medium, where the producer cell produces the third nucleic acid, packaged in a pseudotyped vector, in the cell culture supernatant. In some embodiments, the culture medium will include sodium butyrate.

Compositions and Formulations

The present invention further provides composition comprising a subject pseudotyped retroviral vector. Compositions comprising a subject pseudotyped retroviral vector will in many embodiments include one or more of: a salt, e.g., NaCl, MgCl, KCl, MgSO$_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like.

In some embodiments, a subject composition comprises a pseudotyped retroviral vector and a pharmaceutically acceptable excipient. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20$^{th}$ edition, Lippincott, Williams, & Wilkins; Pharmaceutical Dosage Forms and Drug Delivery Systems (11029) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

Formulations Suitable for Injection

A subject pseudotyped retroviral vector is in some embodiments formulated into a preparation suitable for injection (e.g., subcutaneous, intravenous, intramuscular, intradermal, transdermal, or other injection routes) by dissolving, suspending or emulsifying the agonist in an aqueous solvent (e.g., saline, and the like) or a nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Formulations for Enteral Delivery

For oral preparations, a subject pseudotyped retroviral vector is formulated alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives, and flavoring agents.

For enteral delivery, a subject formulation will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

Purification

The present invention further provides methods of purifying pseudotyped recombinant retroviral vectors; and purified pseudotyped recombinant retroviral virions. The methods apply to subject pseudotyped recombinant retroviral virions that comprises a recombinant envelope protein comprising a metal ion affinity peptide. Purification methods provided by the present invention generally involve contacting a sample containing a subject pseudotyped recombinant retroviral virion with an immobilized metal ion affinity resin under conditions which favor binding of the metal ion affinity peptide portion of the recombinant envelope protein to the immobilized metal, and eluting the bound pseudotyped recombinant retroviral virion. One or more washing steps may optionally be included to remove undesired components of the sample applied to the resin. Two or more different resins may be used.

Using a method as described herein, a subject pseudotyped recombinant retroviral virion is purified to a desired degree, depending on the application. In some embodiments, a subject pseudotyped recombinant retroviral virion purified using a subject method is at least about 60%, at least about 70%, at least about 80%, at least about 85%, at least about 90%, at least about 95%, at least about 98%, at least about 99%, or more, pure, e.g., free of macromolecules, or particle other than the pseudotyped recombinant retroviral virion, found in a sample comprising the pseudotyped recombinant retroviral virion before the virion is purified.

Metal Ion Affinity Resins

Any of a variety of available metal ion chelating resins can be used. In general, a metal ion chelating resin includes a carrier matrix, optionally a spacer, and a moiety that comprises a metal ion, e.g., an organic ligand that immobilizes a metal ion. Carrier matrices include, but are not limited to, cross-linked dextrans, polystyrenes, nylon, agarose, and polyacrylamides. Metal chelating ligands include, but are not limited to, carboxymethyl aspartate (CM-Asp); iminodiacetic acid (IDA); tris(carboxymethyl)ethylene diamine (TED); nitrilo triacetic acid (NTA). Several of these are commercially available.

The metal ion chelating resin can be provided in the form of a chromatography column, e.g., wherein the resin is packed in a column. The resin can also comprise a matrix that is a solid support of any shape or configuration. Thus, the term "resin," as used herein, refers to a resin comprising a matrix in any form, e.g., a bead, a sheet, a well, and the like.

Metal ions metal ions can be divided into three categories (hard, intermediate and soft) based on their preferential reactivity towards nucleophiles. To the group of hard metal ions belong $Fe^{3+}$, $Ca^{2+}$ and $Al^{3+}$ which show a preference for oxygen. Soft metal ions such as $Cu^+$, $Hg^{2+}$, $Ag^+$, etc, prefer sulfur. Intermediate metal ions ($Cu^{2+}$, $Ni^{2+}$, $Zn^{2+}$, $Co^{2+}$) coordinate nitrogen, oxygen and sulfur. Histidine residues bind intermediate metal ions with high affinity. The binding constant of an average protein with a single histidyl residue is about $4.5 \times 10$ $M^{-1}$.

In some embodiments, a metal ion chelate resin is a $Co^{2+}$-immobilizing resin. Such resins are described in U.S. Pat. No. 5,962,641.

In some embodiments, the invention provides methods of purifying a subject pseudotyped retroviral vector using multiple metal ion affinity resins, e.g., two or more different metal ion affinity resins. The multiple metal ion affinity resins can be provided in the same column, e.g., mixed together, or layered one on top of the other; or provided in two separate, tandem columns. In some embodiments, a first metal ion affinity resin comprises a matrix, a first metal ion chelating ligand, and a first immobilized metal ion, wherein the first metal ion is selected from the group consisting of $Fe^{3+}$, $Ca^{2+}$ and $Al^{3+}$; and a second metal ion affinity resin comprises a matrix, a second metal ion chelating ligand, and a second immobilized metal ion, wherein the second immobilized metal ion is selected from the group consisting of $Cu^{2+}$, $Ni^{2+}$, $Zn^{2+}$, $Co^{2+}$. In other embodiments, a first metal ion affinity resin comprises a matrix, a metal ion chelating ligand, and a first immobilized metal ion, wherein the first metal ion is selected from the group consisting of $Fe^{3+}$, $Ca^{2+}$ and $Al^{3+}$; and a second metal ion affinity resin comprises a matrix, a metal ion chelating ligand, and a second immobilized metal ion, wherein the second immobilized metal ion is selected from the group consisting of $Cu^{2+}$, $Ni^{2+}$, $Zn^{2+}$, $Co^{2+}$. In these embodiments, the first and second metal ion affinity resins comprise the same metal ion ligand. In some embodiments, a sample comprising a fusion protein is applied to a first resin, the resin washed to remove unbound components of the sample, bound fusion protein eluted from the first resin, and the eluted fusion protein applied to the second resin, followed by washing and eluting steps.

Conditions for Binding

The conditions under which a sample comprising a subject pseudotyped retroviral vector is applied to a metal ion affinity resin will vary according to various parameters, including the properties of the undesired components of the protein sample, etc. Generally, the sample is applied to the metal ion affinity resin, and the resin is equilibrated with a solution. "Conditions for binding" include a condition of the sample being applied, as well as any equilibration conditions. Those skilled in the art can readily determine appropriate conditions for binding of a subject pseudotyped retroviral vector in a sample to a metal ion affinity resin, based on known and determined properties of the metal ion binding peptide, etc. Conditions may be chosen such that a subject pseudotyped retroviral vector retains its native conformation and/or activity. Salt concentrations suitable for applying a sample comprising a subject pseudotyped retroviral vector to a metal ion affinity resin range from about 0.01 M NaCl to about 3 M NaCl, from about 0.05 M NaCl to about 1.5 M NaCl, from about 0.1 M NaCl to about 1.0 M NaCl, or from about 0.2 M NaCl to about 0.5 M NaCl. The pH conditions suitable for applying a sample comprising a subject pseudotyped retroviral vector to a metal ion affinity resin range from about 3.5 to about 11, from about 4.0 to about 10.0, from about 4.5 to about 9.5, from about 5.0 to about 9.0, from about 5.5 to about 8.5, from about 6.0 to about 8.0, or from about 6.5 to about 7.5. Temperature conditions suitable for applying a sample comprising a subject pseudotyped retroviral vector to a metal ion affinity resin range from about 15° C. to about 40° C., from about 20° C. to about 37° C., or from about 22° C. to about 25° C. Various additional substances may be included, including, but not limited to, detergents (e.g., sodium dodecyl sulfate, e.g., from about 0.05% to about 2%); non-ionic detergents, e.g., Tween 20™, and the like; chaotropic agents and denaturants, e.g., urea, and guanidinium HCl; buffers, e.g., Tris-based buffers, borate-based buffers, phosphate-based buffers, imidazole, HEPES, PIPES, MOPS, PIPES, TES, and the like.

Washing

One or more washing steps may be included, to remove undesired components. A washing step may be performed after a subject pseudotyped retroviral vector is immobilized on a resin. The composition and temperature of a washing solution may vary according to the desired result. The optimal composition and temperature of a washing solution can readily be determined by those skilled in the art, based on known properties of the immobilized pseudotyped retroviral vector. Wash solutions may comprise a buffer, and may further comprise additional components, as necessary, including, but not limited to, a detergent.

Eluting

The immobilized pseudotyped retroviral vector can be eluted using a pH gradient; addition of a competitor, e.g., an organic acid, phosphates; addition of a displacer such as imidazole; addition of a metal chelator such as EDTA; and the like.

Genetically Modifying Host Cells

The present invention further provides methods of genetically modifying a host cell (also referred to herein as "target cell" or "target host cell"). The methods generally involve contacting a subject pseudotyped retroviral vector with a target cell. Target cells transduced by ("genetically modified by") a subject pseudotyped retroviral vector may be used to express the heterologous nucleic acid contained within the vector under in vitro, in vivo, or ex vivo conditions.

The term "target cell" includes any cell derivable from a suitable organism which a vector is capable of transfecting or transducing. Examples of target cells include but are not limited to macrophages, endothelial cells or combinations thereof. Further examples include but are not limited to hematopoietic stem cells, neural stem cells, mesenchymal stem cells, embryonic stem cells, lymphocytes, vascular endothelial cells, respiratory epithelial cells, keratinocytes, skeletal and cardiac muscle cells, neurons, cancer cells respiratory airway epithelial cells, hepatocytes, muscle cells, cardiac myocytes, synoviocytes, primary mammary epithelial cells and post-mitotically terminally differentiated non-replicating cells such as macrophages and/or neurons.

Delivery of a Gene Product

The present invention further provides methods of delivering a gene product to an individual. The methods generally involve introducing a subject pseudotyped retroviral vector into an individual.

Generally, a subject pseudotyped recombinant retroviral vector is introduced into a cell using either in vivo or in vitro transduction techniques. If transduced in vitro, the desired recipient cell will be removed from the subject, transduced with a subject pseudotyped recombinant retroviral vector and reintroduced into the subject. Alternatively, syngeneic or xenogeneic cells can be used.

Suitable methods for the delivery and introduction of transduced cells into a subject have been described. For example, cells can be transduced in vitro by combining a subject recombinant retroviral vector with cells e.g., in appropriate media, and screening for those cells harboring the nucleic acid of interest, using conventional techniques such as Southern blots and/or PCR, or by using selectable markers. Transduced cells can then be formulated into pharmaceutical compositions, described more fully below, and the composition introduced into the subject by various techniques, such as by intramuscular, intravenous, subcutaneous and intraperitoneal injection.

For in vivo delivery, a subject recombinant retroviral vector will be formulated into pharmaceutical compositions and will generally be administered parenterally (e.g., administered via an intramuscular, subcutaneous, intratumoral, transdermal, intrathecal, etc., route of administration).

Pharmaceutical compositions will comprise sufficient genetic material to produce a therapeutically effective amount of the gene product of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Appropriate doses will depend on the mammal being treated (e.g., human or nonhuman primate or other mammal), age and general condition of the subject to be treated, the severity of the condition being treated, the particular therapeutic protein in question, its mode of administration, among other factors. An appropriate effective amount can be readily determined by one of skill in the art.

Thus, a "therapeutically effective amount" will fall in a relatively broad range that can be determined through standard laboratory experiments and/or clinical trials. For example, for in vivo delivery, a therapeutically effective dose will be on the order of from about $10^6$ to about $10^{15}$ of the recombinant retroviral vector, e.g., from about $10^8$ to $10^{12}$ recombinant retroviral vector. For in vitro transduction, an effective amount of recombinant retroviral vector to be delivered to cells will be on the order of from about $10^8$ to about $10^{13}$ of the recombinant retroviral vector. Other effective dosages can be readily established by one of ordinary skill in the art through routine trials establishing dose response curves.

Dosage treatment may be a single dose schedule or a multiple dose schedule. Moreover, the subject may be administered as many doses as appropriate. One of skill in the art can readily determine an appropriate number of doses.

In some embodiments, the present invention provides methods of delivering a gene product to a stem cell. In these embodiments, a subject recombinant retroviral vector is introduced into a stem cell, either in vitro or in vivo. Stem cells of interest include hematopoietic stem cells and progenitor cells derived therefrom (U.S. Pat. No. 5,061,620); neural crest stem cells (see Morrison et al. (1999) Cell 96:737-749); adult neural stem cells or neural progenitor cells; embryonic stem cells; mesenchymal stem cells; mesodermal stem cells; etc. Other hematopoietic "progenitor" cells of interest include cells dedicated to lymphoid lineages, e.g. immature T cell and B cell populations.

Purified populations of stem or progenitor cells may be used. For example, human hematopoietic stem cells may be positively selected using antibodies specific for CD34, thy-1; or negatively selected using lineage specific markers which may include glycophorin A, CD3, CD24, CD16, CD14, CD38, CD45RA, CD36, CD2, CD19, CD56, CD66a, and CD66b; T cell specific markers, tumor specific markers, etc. Markers useful for the separation of mesodermal stem cells include FcγRII, FcγRIII, Thy-1, CD44, VLA-4α, LFA-1, HSA, ICAM-1, CD45, Aa4.1, Sca-1, etc. Neural crest stem cells may be positively selected with antibodies specific for low-affinity nerve growth factor receptor (LNGFR), and negatively selected for the markers sulfatide, glial fibrillary acidic protein (GFAP), myelin protein $P_o$, peripherin and neurofilament. Human mesenchyrnal stem cells may be positively separated using the markers SH2, SH3 and SH4.

The cells of interest are typically mammalian, where the term refers to any animal classified as a mammal, including humans, domestic and farm animals, and zoo, laboratory, sports, or pet animals, such as dogs, horses, cats, cows, mice, rats, rabbits, etc. In some embodiments, the stem cell is a human stem cell.

The cells which are employed may be fresh, frozen, or have been subject to prior culture. They may be fetal, from a neonate, or from an adult. Hematopoietic cells may be obtained from fetal liver, bone marrow, blood, particularly G-CSF or GM-CSF mobilized peripheral blood, or any other conventional source. The manner in which the stem cells are separated from other cells of the hematopoietic or other lineage is not critical to this invention. As described above, a substantially homogeneous population of stem or progenitor cells may be obtained by selective isolation of cells free of markers associated with differentiated cells, while displaying epitopic characteristics associated with the stem cells.

Any of a variety of proteins can be delivered to an individual using a subject method. Suitable proteins include, but are not limited to, an interferon (e.g., IFN-γ, IFN-α, IFN-β, IFN-ω; IFN-τ); an insulin (e.g., Novolin, Humulin, Humalog, Lantus, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β); and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); and the like), including an antigen-binding fragment of a monoclonal antibody; a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®); IL-3, IL-4, IL-5, IL-6, IL-7, IL-8, IL-9; etc.); a growth factor (e.g., Regranex® (beclapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a soluble receptor (e.g., a TNF-α-binding soluble receptor such as Enbrel® (etanercept); a soluble VEGF receptor; a soluble interleukin receptor; a soluble γ/δ T cell receptor; and the like); an enzyme (e.g., α-glucosidase; Cerazyme®) (imiglucarase; β-glucocerebrosidase, Ceredase® (alglucerase); an enzyme activator (e.g., tissue plasminogen activator); a chemokine (e.g., IP-10; Mig; Groα/IL-8, RANTES; MIP-1α; MIP-1β; MCP-1β; PF-4; and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like. Proteins that can be delivered using a subject method also include a functional fragment of any of the aforementioned proteins; and functional variants of any of the aforementioned proteins.

In some embodiments, a therapeutically effective amount of a protein is produced in the mammalian host. Whether a therapeutically effective amount of a particular protein is produced in the mammalian host using a subject method is readily determined using assays appropriate to the particular protein. For example, where the protein is EPO, hematocrit is measured.

Where a subject recombinant retroviral vector encodes an antigenic protein, suitable antigenic proteins that can be delivered to an individual using a subject method include, but are not limited to, tumor-associated antigens, autoantigens ("self" antigens), viral antigens, bacterial antigens, protozoan antigens, and allergens; and antigenic fragments thereof. In some embodiments, a cytotoxic T lymphocyte (CTL) response to the subject recombinant retroviral vector-encoded antigenic protein will be induced in the mammalian host. In other embodiments, a humoral response to the subject recombinant retroviral vector-encoded antigenic protein will be induced in the mammalian host, such that antibodies specific to the antigenic protein are generated. In many embodiments, a TH1 immune response to the subject recombinant retroviral vector-encoded antigenic protein will be induced in the mammalian host. Whether an immune response to the antigenic protein has been generated is readily determined using well-established methods. For example, an enzyme-linked immunosorbent assay can be used to determine whether antibody to an antigenic protein has been generated. Methods of detecting antigen-specific CTL are well known in the art. For example, a detectably labeled target cell expressing the antigenic protein on its surface is used to assay for the presence of antigen-specific CTL in a blood sample.

Nucleic acids that can be delivered to an individual using a subject method include non-translated RNAs, such as an anti-sense RNA, a ribozyme, an RNAi and an siRNA. In some embodiments, a therapeutically effective amount of the non-translated RNA is produced in the mammalian host. Whether a therapeutically effective amount of a non-translated RNA has been delivered to a mammalian host using a subject method is readily determined using any appropriate assay. For example, where the gene product is an siRNA that inhibits HIV, viral load can be measured.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Generation of Recombinant VSV-G Proteins

Materials and Methods

Cell lines. HEK 293T and 293 cells were cultured in IMDM supplemented with 10% FBS at 37° C. and 5% $CO_2$, except when packaging vectors at 30° C. (described below). The 293-gag-pol cell line was constructed by co-transfection of pCMV gag-pol, a plasmid that expresses MoMLV gag-pol from the CMV promoter, and a plasmid that expresses the neomycin resistance gene into 293 cells. Single colonies were expanded and tested for their ability to package infectious retrovirus upon transfection of pCLPIT GFP, a retroviral construct (Ignowski Schaffer (2004) Biotechnol Bioeng 86:827-34) that expresses enhanced green fluorescent protein (eGFP, BD Clontech, Palo Alto, Calif.), and pcDNA3 IVS VSV-G, a plasmid based on pcDNA3 that expresses the human β-globin intron and wild-type (WT) VSV-G from the CMV promoter.

Construction of the pCLPIT VSV-G-$His_6$ library and clonal helper plasmids. The kanamycin resistance ($kan^R$) gene was randomly inserted into a plasmid containing vsv-g (Indiana strain) using the MGS kit (Finnzymes, Espoo, Finland). This plasmid library was digested to excise vsv-g-$kan^R$ fragments, which were subsequently cloned into pCLPIT, allowing for transgene expression to be regulated with doxycycline (Gossen and Bujard (1992) Proc Natl Acad Sci USA 89:5547-51). The $His_6$ insert was constructed by annealing the following oligonucleotides: 5'-AGTCGGGCC CACCACCACCATCATCATGGGGCCCAGTC-3 (SEQ ID NO:32) and 5'-GACTGGGCCCCATGATGATGGTGGTG- GTGGGCCCGACT-3' (SEQ ID NO:33), where the region encoding the $His_6$ is underlined. The pCLPIT VSV-G-Kan$^R$ library was digested with NotI before ligation to $His_6$ inserts digested with PspOMI. The ligation product was digested with NotI before transformation to eliminate backbone religations. The total library size was estimated by colony counting of a dilution of each transformation. The plasmid library and individual clones were digested with BstXI, which cleaves once in each the insert and backbone, to confirm insertion number and diversity.

Individual VSV-G-$His_6$ sequences were constructed using splicing by overlap extension PCR, cloned into pcDNA3 IVS, and verified by sequencing analysis (Ho et al. (1989) Gene 77:51-9). Oligonucleotides were designed to include the sequence for the $His_6$ insert and a short portion of the vsv-g sequence neighboring the desired site of insertion.

Viral vector production Vectors were packaged by calcium phosphate transfection of 293T cells in 10 cm plates. For the VSV-G-$His_6$ library, 10 μg pCLPIT VSV-G-$His_6$, 6 μg pCMV gag-pol, and 4 μg pcDNA3 IVS VSV-G were first transfected in the presence of doxycyline to suppress the expression of VSV-G-$His_6$ proteins. For the clonal analysis, 4-8 μg individual pcDNA3 IVS VSV-G-$His_6$ constructs were transfected with 8-10 μg pCLPIT GFP and 6 μg pCMV gag-pol to create retroviral vectors, or 3.5 μg VSV-G-$His_6$ constructs with 10 μg pHIV CS TRIP CG (a lentiviral construct based on pHIV CS CG (Miyoshi et al. (1998) J Virol 72:8150-7) that contains the central polypurine tract), 5 μg pMDLg/pRRE (Dull et al. (1998) J Virol 72:8463-71), and 1.5 μg pRSV Rev for lentiviral vectors. Culture medium was changed after 12 h, and 36 h later, viral supernatant collected and concentrated by ultracentrifugation in a SW41 rotor (Beckman Coulter, Fullerton, Calif.) at 50,000×g for 1.5 h at 4° C. before resuspension in PBS (pH 7.0). To package clones at 30° C., cells were transfected as above and incubated at 30° C. 12 h after transfection. Production of viral supernatant for use in vivo was performed as above. For ultracentrifugation enrichment, supernatant was first concentrated through a 20% sucrose in PBS cushion by ultracentrifugation at 50,000×g for 1.5 h at 4° C. Pellets were resuspended in 10 ml phosphate-buffered saline (PBS), and ultracentrifuged again prior to resuspension in PBS. For column purified vectors, the column eluate was diluted into 8 ml PBS, concentrated as above, and resuspended in fresh PBS to remove any imidazole.

To determine the titer of CLPIT VSV-G-$His_6$ and CLPIT VSV-G stocks, serial dilutions of concentrated virus was used to infect 293T cells with 8 μg/ml polybrene. After 24 h, cells were washed and cultured in the presence of 1 μg/ml puromycin for an additional 48 h. Proliferating cells were counted using the WST-1 assay (Roche, Indianapolis, Ind.), and the percentage of puromycin-resistant cells was calculated by comparison to control cells. To titer eGFP expressing vectors, 293T cells were infected with at least 3 different volumes of vector supernatant or concentrate with polybrene for 24 h. Cells were assayed for eGFP expression by flow cytometry 48 h after infection. In both assays, MOIs were first estimated assuming a Poisson distribution for infection. Titers were then calculated by linear regression of samples for which the MOI was less than 1. Error bars represent the SE of the linear regression for representative samples.

Immunofluorescence detection of VSV-G. pCLPIT VSV-G-$His_6$ or pCLPIT VSV-G plasmids were transfected into 293T cells. 16 h after transfection, cells were washed, fixed, and blocked before incubation with mouse anti-VSV-G antibody P5D4 (1:1000; Sigma, St. Louis, Mo.), which recognizes the C-terminus, in the presence of 0.3% Triton X-100 to detect intracellular expression or the I1 antibody (1:100) (Lefrancios and Lyles (1982). Virology 121:157-67) without Triton X-100 to detect surface expression. Cells were washed and incubated with donkey anti-mouse AlexaFluor 488 (1:250; Molecular Probes, Eugene, Oreg.) secondary antibody and were counterstained with TO-PRO-3 (1:2000; Molecular Probes), before imaging by fluorescent confocal microscopy (Leica Microsystems, Wetzlar, Germany). Recognition with the conformation-specific I1 antibody confirms that proteins express a correctly folded epitope: Equivalent results were seen using the I14 antibody (Lefrancois and Lyles (1982) supra).

Western blot detection of Ni-NTA binding. Concentrated vectors were lysed in RIPA buffer and immunoprecipitated using the P5D4 antibody. Proteins were separated by sodium dodecyl sulfate-polyacrylamide gel electrophoresis (SDS-PAGE) and transferred to a nitrocellulose blot. The blot was blocked in TBS with 1 mg/ml lysozyme (Sigma) and incubated in 1 μM Ni-NTA-biotin (gift from Ravi Kane), 10 mM imidazole, and 1 μg/ml streptavidin-HRP (Amersham Biosciences, Piscataway, N.J.). Bands were detected by ECL detection assay (Amersham Biosciences).

Library selection. Vectors containing CLPIT VSV-G-$His_6$ library genomes pseudotyped with WT VSV-G were used to infect 293-gag-pol cells at an MOI<0.1. Cells were selected using 1 μg/ml puromycin and propagated in the presence of 100 ng/ml doxycycline to prevent continuous production of virus. To rescue virus, infected 293-gag-pol cells were grown to confluence without doxycycline, and 5 mM sodium butyrate was added 2 d before viral harvest (Kafri et al. (1999) J Virol 73:576-84). Harvested virus (round 1 of selection) was then used to infect at least 106 naïve 293-gag-pol cells at an MOI<0.1, and cells were propagated as above. This process was repeated for each successive round of selection. To select for Ni-NTA binding, vectors were purified with Ni-NTA (described below) before infection of naïve cells. To identify selected sequences, cellular genomic DNA or viral genomic RNA was isolated using the Qiagen Genomic Tip 500/G or Qiamp Viral RNA kit (Qiagen, Palo Alto, Calif.), respectively. VSV-G-$His_6$ sequences were amplified by PCR and inserted into a plasmid before sequencing.

Ni-NTA purification of viral vectors. 500 μl of 50% Ni-NTA Agarose (Qiagen) was rinsed with PBS (pH 7.0) and incubated with 300-600 μl of concentrated viral stocks with gentle agitation at 4° C. for 1 h. The mixture of virus and beads was loaded onto a plastic column (Kontes, Vineland, N.J.) before washing with 3 ml of 50 mM imidazole in PBS and elution with 1.5-2 ml of 250 mM imidazole in PBS.

Equivalent volumes of each column fraction from a representative purification procedure were separated by SDS-PAGE. Proteins were detected using the SilverQuest kit (Invitrogen, Carlsbad, Calif.). The IMDM and viral supernatant samples were diluted 10-fold to prevent oversaturation of the silver stain signal. Protein concentrations in stocks representing a 20-fold concentration of viral supernatant by conventional or column purification were quantified using the BCA assay (Pierce Biotechnology, Rockford, Ill.). DNA concentrations in those stocks were quantified by spectrofluorometry after incubation with SYBR Green dsDNA dye (Molecular Probes).

Animal injections and expression analysis. Animal protocols were approved by the UCB Animal Care and Use Committee in accordance with NIH guidelines. Anesthetized adult female Fischer-344 rats were injected with either lentiviral vectors pseudotyped with G-19$LH_6$ (n=3 animals) or G-24$LH_6$ (n=3) that had been purified on a Ni-NTA column, or vectors pseudotyped with G-24$LH_6$ (n=3) or WT VSV-G (n=2) that were purified by ultracentrifugation only. Animals received 3 μl of high titer vector preparations ($8×10^8$-$1.2×10^9$ IU/ml) into the striatum by stereotaxic injection (coordinates from bregma: AP: +0.2; ML: ±3.5; DV: −4.5 from dura with nose bar at +3 mm). After 2 weeks, brains were harvested, and coronal sections (40 μm) were taken as previously described (Lai et al (2003) Nat Neurosci 6:21-7). Primary antibodies included rabbit anti-GFP (1:2000 dilution; Molecular Probes), guinea pig anti-GFAP (1:1000; Advanced Immunochemical, Long Beach, Calif.); mouse anti-neuN, mouse anti-OX8, mouse anti-ED1 (1:100; Chemicon, Temecula, Calif.). Corresponding AlexaFluor 488, 546 or 633 conjugated secondaries (1:250; Molecular Probes) were used, and some sections were counterstained with TO-PRO-3 (1:2000) before imaging by confocal microscopy. The area of eGFP expression in 22-26 evenly spaced sections from each animal was measured, and total volume of eGFP expression in each sample was estimated using modified stereological methods. Errors represent the SEM of each preparation. Results were analyzed for statistical significance using the ANOVA test between all vector samples.

Results

Construction of the VSV-G-His$_6$ Library. A library of vsv-g-kan$^R$ insertion mutants was constructed using MuA transposase and a modified transposon insert carrying a kanamycin resistance gene (kan$^R$). Haapa et al. (1999) Nucleic Acids Res 27:2777-84. The resulting vsv-g-kan$^R$ gene library was cloned into the retroviral vector construct, pCLPIT, which also expresses a puromycin resistance gene (Ignowski and Schaffer (2004) supra), and kan$^R$ was then replaced with His$_6$ tag sequence to create pCLPIT VSV-G-His$_6$ (FIG. 1A). The sequence of the 13 amino acid (aa) insert (SEQ ID NO:34) is dependent on the 5 neighboring host nucleotides that are duplicated during the transposition reaction (Haapa et al. (1999) supra) (FIG. 1B). FIG. 1B provides the amino acid sequence (SEQ ID NO:34) of the His$_6$ insert; and the nucleotide sequence (SEQ ID NO:35) encoding the His$_6$ insert. Restriction digest analyses of the pooled plasmid library and randomly selected clones confirmed that insertions occurred at a diverse number of sites and that each clone had a single insertion (FIG. 1C). After accounting for insertions into non-coding regions, the library was estimated to contain over $2.4 \times 10^4$ independent insertions into the 1.6 kb VSV-G cDNA. A similar control vector, pCLPIT VSV-G, was constructed, which expresses wild-type (WT) VSV-G.

FIG. 1A-C. VSV-G-His$_6$ library design. (A) Structure of the pCLPIT VSV-G-His$_6$ vector, which expresses the VSV-G-His$_6$ library from a tetracycline regulatable promoter and puromycin resistance from the viral LTR. (B) Peptide and DNA sequences for the His$_6$ insert after insertion. $X_1$ and $X_2$ will depend on the 5 host nt (N) duplicated during insertion. The digested insert sequence is underlined and in bold. (C) The pCLPIT VSV-G-His$_6$ plasmid library and clones were cut once in the His$_6$ insertion and once in pCLPIT. Successful insertions into vsv-g yield fragments of 1.6-3.2 kb in size. Lanes: 1, pCLPIT VSV-G; 2, pCLPIT VSV-G-His$_6$ library; 3-12, randomly selected pCLPIT VSV-G-His$_6$ clones.

Immunostaining of cells transfected with pCLPIT VSV-G-His$_6$ or pCLPIT VSV-G plasmids revealed VSV-G expression intracellularly and on the cell surface in both populations, indicating that members of the vsv-g-his$_6$ library can express VSV-G and that at least some of these variants are trafficked to the cell surface (FIG. 2A,B). Western blot analysis of VSV-G-His$_6$-pseudotyped retroviral vectors using a Ni-NTA probe demonstrated that His$_6$-containing VSV-G proteins could be incorporated into retroviral particles (FIG. 2C).

Figure 2B:
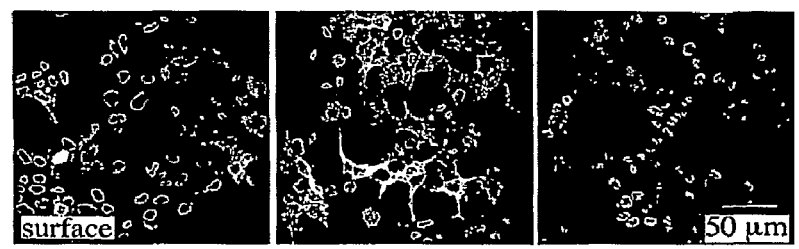
Figure 2C:
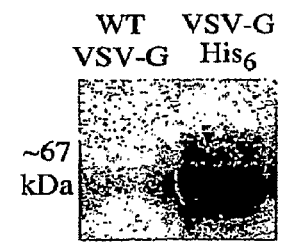

FIG. 2A-C. Expression of library proteins. (A, B) Immunostaining of cells transfected with pCLPIT VSV-G-His$_6$ or pCLPIT VSV-G to detect intracellular (A) and surface (B) expression of VSV-G (white, 63× objective). Cells are counterstained with TO-PRO-3 (gray). (C) Western blot detection of VSV-G-His$_6$ library proteins binding to Ni-NTA.

Selection of the VSV-G-His$_6$ Library Using Retroviruses. To select insertion mutants that retained the ability to mediate cellular infection, the viral library was serially passaged on 293 cells stably expressing retroviral gag-pol (FIG. 3A). Viral titers were determined at each round of infection and rescue (FIG. 3B). Importantly, sequencing a sample of the library after three selection rounds showed that at least three sites in the signal peptide and three in the extracellular domain allowed the 13 aa insertion. Insertions in the signal peptide likely yield proteins identical to WT (wild-type) in their mature form and were thus not pursued. Three other sites before aa positions 19, 24, and 26 (with the start codon as position 1), however, have not been previously identified. Next, to isolate insertion mutants that presented functionally active peptides, the selection protocol was repeated, but the viral library was purified on a Ni-NTA column before infecting cells. This procedure was repeated until the majority of the viral library loaded was present in the final eluate. Analysis of these sequences revealed that a single clone containing a His$_6$ insertion, in frame in site 19 was dominant within the population.

FIGS. 3A and 3B. VSV-G-His$_6$ library selection. (A) Schematic of library selection using retroviral infection of cells. (B) Viral titers for each round of selection for replication.

Purification of VSV-G-His$_6$-Pseudotyped Vectors by Ni-NTA Chromatography. To assess the ability of VSV-G-His$_6$ variants to pseudotype retroviral and lentiviral vectors, a His$_6$ tag was inserted into all three novel sites identified from the selection, as well as in site 17, the N-terminus of the mature protein, and in two previously identified sites, the temperature sensitive site 25 (Guibing a et al. (2004) Mol Ther 9:76-84) and site 191 (Schlehuber and Rose (2004) J Virol 78:5079-87). Furthermore, to explore the effects of different amino acid linkers flanking the His$_6$ tag, multiple variants at two of the sites were constructed (Table 1).

TABLE 1

VSV-G-His$_6$ clone sequences[a,b].

| Name | Amino acid sequence |
|---|---|
| G-17_H$_6$ | MKCLLYLAFLFIGVNCHHHHHHKFTIVFPHNQKGN . . . (SEQ ID NO: 36) |
| G-173H$_6$ | MKCLLYLAFLFIGVNCHHHHHHGGSKFTIVFPHNQKGN . . . (SEQ ID NO: 37) |
| G-17L6H$_6$ | MKCLLYLAFLFIGVNCHHHHHHGGSGGSKFTIVFPHNQKGN . . . (SEQ ID NO: 38) |
| G-19LH$_6$ | MKCLLYLAFLFIGVNCKFSGGHHHHHHGGSTIVFPHNQKGN . . . (SEQ ID NO: 39) |
| G-24_H$_6$ | MKCLLYLAFLFIGVNCKFTIVFPHHHHHHHNQKGN . . . (SEQ ID NO: 40) |
| G-24LH$_6$ | MKCLLYLAFLFIGVNCKFTIVFPSGGHHHHHHGGSHNQKGN . . . (SEQ ID NO: 41) |
| G-25LH$_6$ | MKCLLYLAFLFIGVNCKFTIVFPHSGGHHHHHHGGSNQKGN . . . (SEQ ID NO: 42) |
| G-26LH$_6$ | MKCLLYLAFLFIGVNCKFTIVFPHNSGGHHHHHHGGSQKGN . . . (SEQ ID NO: 43) |
| G-191LH$_6$ | . . . DYKVKSGGHHHHHHGGSGLCDSN . . . (SEQ ID NO: 44) |
| WT VSV-G | [1]MKCLLYLAFL[11]FIGVNCKFTIV[21]FPHNQKGN . . . [186]DYKVK[191]GLCDSN . . . (SEQ ID NO: 45) |

[a]Each clone is designated by the site of insertion and presence of a linker peptide (L). Residue positions are provided in the sequence for WT VSV-G.
[b]Newly introduced amino acids are underlined.

Figure 4A:
FIGS. 4A and 4B depict immunofluorescence detection of VSV-G-His$_6$ clones.

All variants were inserted into a helper plasmid for vector production, and plasmid transfections demonstrated that the new mutants expressed VSV-G proteins that could be trafficked to the surface of cells (FIG. 4A,B).

Figure 4B:
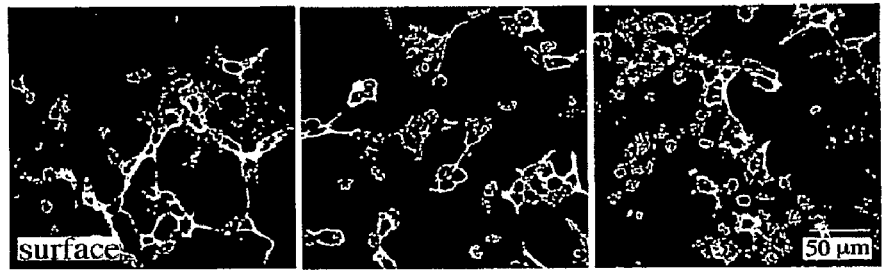

FIGS. 4A and 4B. Immunofluorescence detection of VSV-G-His$_6$ clones. Detection of (A) intracellular and (B) surface expression of VSV-G (white) from individual VSV-G-His$_6$ clones (63× objective). Cells are counterstained with TO-PRO-3 (gray).

Figures 5A, 5B, 5C, 5D:
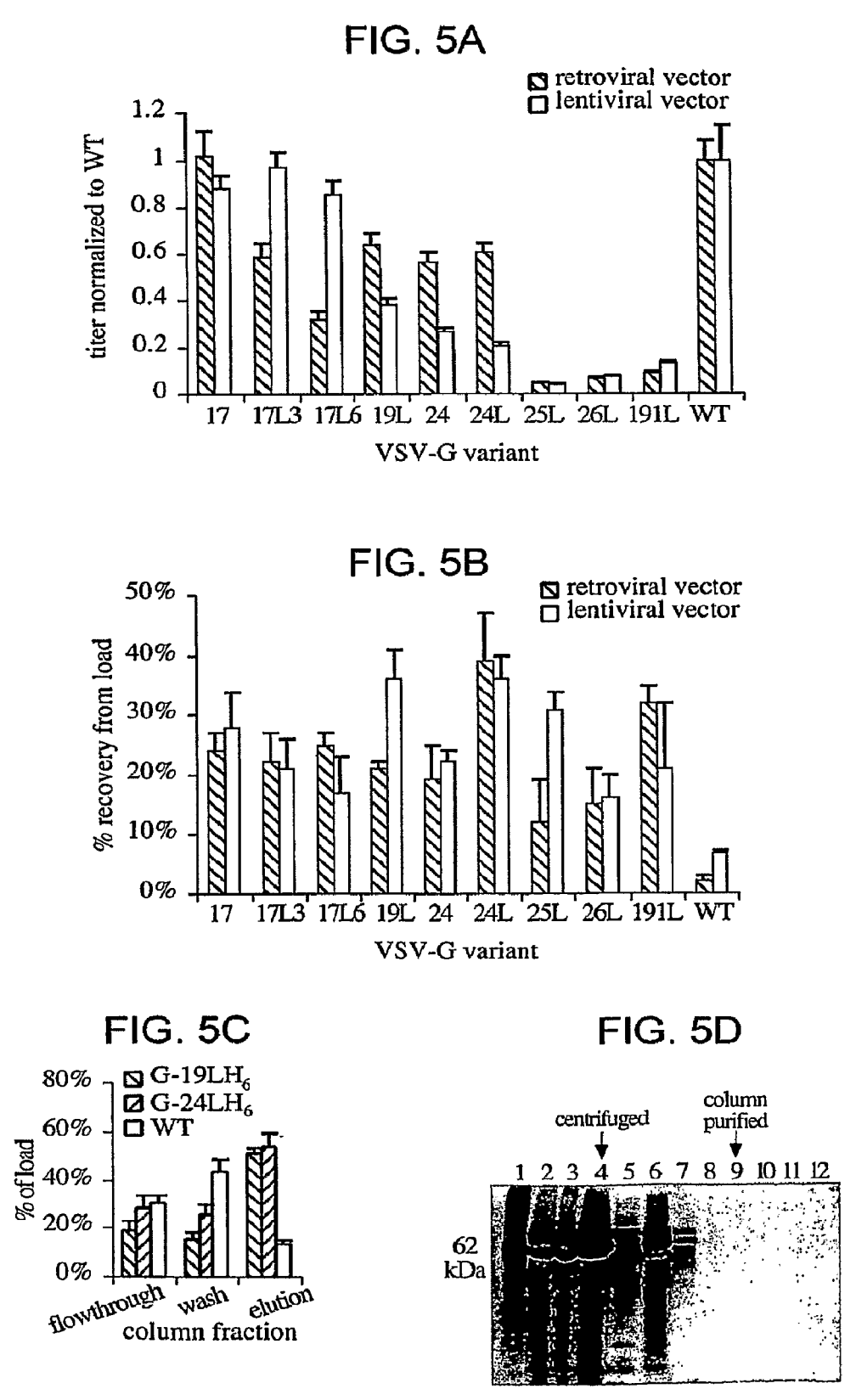

All of the novel VSV-G-His$_6$ helper constructs successfully packaged retroviral and lentiviral vectors eGFP, and many had titers comparable to vectors packaged with WT VSV-G (FIG. 5A). Clone G-25LH$_6$, with an insert at the previously identified temperature sensitive site 25, did not yield infectious retroviruses when packaged at 37° C., but was able to produce retroviral vectors at 30° C. as previously described (Guibing a et al. (2004) supra). Typical titers of viral supernatant for these vectors using WT VSV-G are 3-5×10$^6$ IU/ml for retrovirus and 1-3×10$^7$ IU/ml for lentivirus. Importantly, most variants bound to a Ni-NTA column at levels substantially higher than WT VSV-G (FIG. 5B). Two of the variants, G-19LH$_6$ and G-24LH$_6$, were then used to optimize parameters such as binding volume, incubation time, buffer pH, ratio of virus to Ni-NTA resin, and wash and elution conditions. Using an optimized procedure, the total virus recovery exceeded 50% (FIG. 5C).

Column purification dramatically reduced protein contaminants compared to purification by ultracentrifugation through a sucrose cushion, a conventional method for enriching vectors (Baekelandt et al. (2003) Gene Ther 10:1933-40) (FIG. 5D). Protein and DNA concentrations in the column purified preparations were below the detection limit of their respective assays, so estimates are conservatively based on the minimum values of 25 μg/ml and 10 ng/ml, respectively. For vector stocks 20-fold more concentrated than the original viral supernatant, the ultracentrifugation-enriched virus had only a 5-fold and a 2.7-fold reduction in protein and DNA concentrations compared to the crude viral supernatant. In stark contrast, the column purified virus had at least 250-fold and 700-fold reduced protein and DNA concentrations, resulting in an overall reduction in protein and DNA contamination by over 5,000-fold and 14,000-fold, respectively.

FIG. 5A-D. Column purification of VSV-G-His$_6$-pseudotyped retroviral and lentiviral vectors. (A) Representative titers of retroviral and lentiviral vectors expressing eGFP pseudotyped with VSV-G-His$_6$ variants. Results for the G-25LH$_6$-pseudotyped retroviral vector reflect packaging at 30° C. All other vectors were produced at 37° C. (B) Recovery of vectors pseudotyped with VSV-G-His$_6$ variants after NI-NTA purification. (C) Optimized purification profile of G-19LH$_6$ and G-24LH$_6$-pseudotyped lentiviral vectors. (D) Silver staining of column fractions. Lanes: 1, marker; 2, IMDM+10% FBS (1:10 dilution); 3, vector supernatant (1:10 dilution); 4, ultracentrifuged virus; 5, column flowthrough; 6-8, successive washes; 9-12, successive eluates.

Expression of VSV-G-His$_6$-Pseudotyped Vectors in vivo. To evaluate the performance of column purified VSV-G-His$_6$-pseudotyped vectors in vivo, column and conventionally purified lentiviral vectors expressing eGFP were injected into the striatum of adult rats. Two weeks after injection, eGFP expression was observed in every animal, and the cellular tropism of the VSV-G-His$_6$-pseudotyped vectors was the same as WT VSV-G-pseudotyped lentiviral vectors, with preferential infection of NeuN positive neurons and modest colocalization with GFAP$^+$ astrocytes (Naldini et al. (1996) Proc Natl Acad Sci USA 93:11382-8). There was no statistically significant difference in the infection spread in the anterior-posterior axis, determined by the number of eGFP$^+$ sections, or the overall volume of spread between any of the vector preparations.

Reduction of Immune Response Using Column Purified Vectors; A safety concern for the use of gene delivery vectors is the potential generation of a patient immune response (Baekelandt et al. (2002) Hum Gene Ther 13:841-53; Tuschong et al. (2002) Hum Gene Ther 13:1605-10). CD8$^+$ T cell and macrophage activation and infiltration within the region of transduced tissue were considerably different between injections using column purified versus conventionally purified virus. Every injection site, including a PBS control, revealed a low level infiltration of immune cells directly around the needle track, a common result of needle insertion. Within high eGFP expressing regions distal from the injection sites, however, animals injected with the column purified vectors had substantially fewer immune cells compared to those injected with conventionally purified preparations, independently of whether the latter vectors were pseudotyped with WT VSV-G or a VSV-G-His$_6$ variant.

Example 2

Recombinant VSVG-RGD and Pseudotyped Viral Particles

Variants of VSVG with insertions of a targeting peptide containing RGD (Arg-Gly-Asp), or a negative control peptide RGE (Arg-Gly-Glu) into position 24 of the VSVG protein were made. RGD binds to integrin receptors on the surface of cells bearing such receptors, while RGE does not. The amino acid sequences at the insertion site are shown in Table 2. The proline-23 is in bold; peptides containing RGE (bold) or RGD (bold) are underlined.

TABLE 2

| Protein | Amino acid sequence at insertion site |
|---|---|
| Wild-type VSVG | MKCLLYLAFLFIGVNCKFTIVPHNQKG (SEQ ID NO: 46) |
| VSVG-RGD6 | MKCLLYLAFLFIGVNCKFTIVP<u>CGRGDSP</u>CHNQKG (SEQ ID NO: 47) |
| VSVG-RGE6 | MKCLLYLAFLFIGVNCKFTIVP<u>CGRGESP</u>CHNQKG (SEQ ID NO: 48) |
| VSVG-RGD14AG | MKCLLYLAFLFIGVNCKFTIVP<u>CQAGTFALRGDNP</u>QGCHNQKG (SEQ ID NO: 49) |
| VSVG-RGE14AG | MKCLLYLAFLFIGVNCKFTIVP<u>CQAGTFALRGENP</u>QGCHNQKG (SEQ ID NO: 50) |
| VSVG-RGD14GA | MKCLLYLAFLFIGVNCKFTIVP<u>CQGATFALRGDNP</u>QGCHNQKG (SEQ ID NO: 51) |
| VSVG-RGE14GA | MKCLLYLAFLFIGVNCKFTIVP<u>CQGATFALRGENP</u>QGCHNQKG (SEQ ID NO: 52) |

The variants—RGD6, RGE6, RGD14AG, RGE14AG, RGD14GA, and RGE14GA—were used to prepare pseudotyped lentiviral vectors and retroviral vectors, as described in Example 1. The infectivity of the pseudotyped particles was assessed. The results are shown in Tables 3-6, below.

Tables 3 and 4 show the ratio of physical particles to infectious particles of VSVG-RGD pseudotyped lentiviral vectors (Table 3) and VSVG-RGE pseudotyped retroviral vectors (Table 4). Several different cell types were used: 293T; B16F10 (ATCC CRL-5475); TF-1 (ATCC CRL-2003); and MO7E (a human megakaryoblastic leukemia cell line).

TABLE 3

| | \multicolumn{7}{c}{Lentiviral Vectors} | | | | | | |
|---|---|---|---|---|---|---|---|
| | wt | RGD6 | RGE6 | RGD14AG | RGE14AG | RGD14GA | RGE14GA |
| 293T | 1.00 ± 0.14 | 0.71 ± 0.11 | 2.10 ± 0.12 | 1.33 ± 0.09 | 2.70 ± 0.22 | 3.44 ± 0.28 | 3.00 ± 0.64 |
| B16F10 | 1.00 ± 0.18 | 2.81 ± 0.56 | 8.45 ± 1.11 | 5.19 ± 0.47 | 54.44 ± 14.24 | 14.70 ± 3.92 | 16.89 ± 4.09 |
| MO7E | 1.00 ± 0.13 | 2.05 ± 0.37 | 6.66 ± 0.67 | 1.87 ± 0.22 | 5.03 ± 0.85 | 5.54 ± 0.79 | 5.91 ± 1.58 |
| TF-1 | 1.00 ± 0.13 | 36.40 ± 6.18 | 98.32 ± 18.20 | 49.31 ± 1.86 | 84.80 ± 22.01 | 44.96 ± 11.70 | 119.44 ± 40.65 |

TABLE 4

| | Retroviral Vectors | | | | | | |
|---|---|---|---|---|---|---|---|
| | wt | RGD6 | RGE6 | RGD14AG | RGE14AG | RGD14GA | RGE14GA |
| 293T | 1.00 ± 0.15 | 4.07 ± 0.26 | 8.28 ± 0.56 | 2.20 ± 0.24 | 8.62 ± 1.07 | 2.52 ± 0.16 | 3.61 ± 0.54 |
| B16F10 | 1.00 ± 0.15 | 11.14 ± 1.31 | 18.36 ± 5.60 | 17.37 ± 2.05 | 52.58 ± 8.72 | 4.24 ± 0.56 | 6.44 ± 0.75 |
| MO7E | 1.00 ± 0.15 | 6.69 ± 0.46 | 13.67 ± 1.93 | 1.52 ± 0.21 | 5.04 ± 0.60 | 6.98 ± 0.97 | 16.69 ± 3.95 |

Tables 5 and 6 show the infectivity of the VSVG variant containing a peptide with the amino acids RGD compared to the infectivity of a corresponding variant with RGE, which lacks the ability to bind an integrin receptor. This relative infectivity ranged from about 1 (no increased infectivity due to the presence of RGD) up to >10 (10-fold increase in infectivity due to the presence of RGD).

TABLE 5

| | Retroviral Vectors | | | | | | |
|---|---|---|---|---|---|---|---|
| | wt | RGD6 | RGE6 | RGD14AG | RGE14AG | RGD14GA | RGE14GA |
| 293T | 1.00 ± 0.15 | 4.07 ± 0.26 | 8.28 ± 0.56 | 2.20 ± 0.24 | 8.62 ± 1.07 | 2.52 ± 0.16 | 3.61 ± 0.54 |
| B16F10 | 1.00 ± 0.15 | 11.14 ± 1.31 | 18.36 ± 5.60 | 17.37 ± 2.05 | 52.58 ± 8.72 | 4.24 ± 0.56 | 6.44 ± 0.75 |
| MO7E | 1.00 ± 0.15 | 6.69 ± 0.46 | 13.67 ± 1.93 | 1.52 ± 0.21 | 5.04 ± 0.60 | 6.98 ± 0.97 | 16.69 ± 3.95 |

TABLE 6

| | Retroviral Vectors | | | | | | |
|---|---|---|---|---|---|---|---|
| | wt | RGD6 | RGE6 | RGD14AG | RGE14AG | RGD14GA | RGE14GA |
| 293T | 1.00 ± 0.15 | 4.07 ± 0.26 | 8.28 ± 0.56 | 2.20 ± 0.24 | 8.62 ± 1.07 | 2.52 ± 0.16 | 3.61 ± 0.54 |
| B16F10 | 1.00 ± 0.15 | 11.14 ± 1.31 | 18.36 ± 5.60 | 17.37 ± 2.05 | 52.58 ± 8.72 | 4.24 ± 0.56 | 6.44 ± 0.75 |
| MO7E | 1.00 ± 0.15 | 6.69 ± 0.46 | 13.67 ± 1.93 | 1.52 ± 0.21 | 5.04 ± 0.60 | 6.98 ± 0.97 | 16.69 ± 3.95 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A nucleic acid comprising a nucleotide sequence encoding a recombinant viral envelope polypeptide, wherein the recombinant viral envelope polypeptide comprises a vesicular stomatitis virus G polypeptide and a heterologous polypeptide, wherein the heterologous polypeptide is inserted between amino acids 16 and 17, between amino acids 18 and 19, or between amino acids 23 and 24 of a wild-type vesicular stomatitis virus G polypeptide, wherein the recombinant envelope polypeptide retains the ability to mediate cellular infection at 37° C.

2. The nucleic acid of claim 1, wherein the recombinant viral envelope polypeptide is of the formula: $A\text{-}X_1\text{—}Y\text{—}X_2\text{—}B$, wherein A is an amino-terminal portion of the vesicular stomatitis virus G polypeptide;

B is a carboxyl-terminal portion of the vesicular stomatitis virus G polypeptide;

Y is a polypeptide heterologous to the vesicular stomatitis virus G polypeptide; and $X_1$ and $X_2$, if present, are linker peptides.

3. The nucleic acid of claim 1, wherein the heterologous polypeptide is a metal ion binding polypeptide.

4. The nucleic acid of claim 1, wherein the heterologous polypeptide is a targeting polypeptide that provides for cell type-specific binding, cell status-specific binding, or tissue-specific binding.

5. The nucleic acid of claim 1, wherein the recombinant viral envelope polypeptide-encoding nucleotide sequence is operably linked to a promoter.

6. The nucleic acid of claim 5, wherein the promoter is an inducible promoter.

7. An expression construct comprising the nucleic acid of claim 1.

8. The nucleic acid of claim 1, wherein the heterologous polypeptide has a length of from about 6 amino acids to about 25 amino acids.

9. The nucleic acid of claim 3, wherein the metal ion binding polypeptide comprises the amino acid sequence $(His)_n$, where n=3-18.

10. The nucleic acid of claim 4, wherein the targeting polypeptide provides for binding to an endothelial cell.

11. The nucleic acid of claim 4, wherein the targeting polypeptide provides for binding to a tumor cell.

12. The nucleic acid of claim 4, wherein the targeting polypeptide provides for binding to a stem cell.

13. The nucleic acid of claim 1, wherein the heterologous polypeptide has a length of from about 6 amino acids to about 100 amino acids.

* * * * *

UNITED STATES PATENT AND TRADEMARK OFFICE
CERTIFICATE OF CORRECTION

PATENT NO. : 8,163,893 B2  
APPLICATION NO. : 12/279171  
DATED : April 24, 2012  
INVENTOR(S) : David Vernon Schaffer et al.

Page 1 of 1

It is certified that error appears in the above-identified patent and that said Letters Patent is hereby corrected as shown below:

In the Specifications

In the Statement Regarding Federally Sponsored Research

Please amend paragraph 0002 as follows:

~~The U. S. government may have certain rights in this invention, pursuant to grant nos. BES-0094015 awarded by the National Science Foundation.~~ <u>This invention was made with government support under BES-0094015 awarded by the National Science Foundation. The government has certain rights in the invention.</u>

Signed and Sealed this  
Sixth Day of August, 2013

Teresa Stanek Rea  
*Acting Director of the United States Patent and Trademark Office*

SEQUENCE LISTING

<160> NUMBER OF SEQ ID NOS: 52

<210> SEQ ID NO 1
<211> LENGTH: 511
<212> TYPE: PRT
<213> ORGANISM: Vesicular stomatitis virus

<400> SEQUENCE: 1

Met Lys Cys Phe Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Gly Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Thr Asp Ile Thr Phe Phe Ser Glu Asp
        195                 200                 205

Arg Glu Leu Ser Ser Leu Gly Lys Glu Gly Thr Gly Phe Arg Ser Asn
    210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

```
Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Gly Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ile Leu Phe Phe Gly Asp Thr Gly Leu Ser Lys
        435                 440                 445

Asn Pro Ile Asp Phe Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile Tyr Leu Tyr Ile Lys Leu Lys His Thr Lys
                485                 490                 495

Lys Arg Gln Ile Tyr Thr Asp Ile Glu Met Asn Arg Leu Gly Arg
            500                 505                 510

<210> SEQ ID NO 2
<211> LENGTH: 1665
<212> TYPE: DNA
<213> ORGANISM: Vesicular stomatitis virus

<400> SEQUENCE: 2
```

| | | | | | |
|---|---|---|---|---|---|
| aacagagatc | gatctgtttc | cttgacacca | tgaagtgctt | tttgtactta | gcttttttat | 60 |
| tcatcggggt | gaattgcaag | ttcaccatag | ttttttccaca | caaccaaaaa | ggaaactgga | 120 |
| aaaatgttcc | ttccaattac | cattattgcc | cgtcaagctc | agatttaaat | tggcataatg | 180 |
| acttaatagg | cacaggctta | caagtcaaaa | tgcccaagag | tcacaaggct | attcaagcag | 240 |
| acggttggat | gtgtcatgct | tccaaatggg | tcactacttg | tgatttccgc | tggtacggac | 300 |
| cgaagtatat | aacacattcc | atccgatcct | tcactccatc | tgtagaacaa | tgcaaggaaa | 360 |
| gcattgaaca | aacgaaacaa | ggaacttggc | tgaatccagg | cttccctcct | caaagttgtg | 420 |
| gatatgcaac | tgtgacggat | gccgaagcag | tgattgtcca | ggtgactcct | caccatgtgc | 480 |
| ttgttgatga | atacacagga | gaatgggttg | attcacagtt | catcaacgga | aaatgcagca | 540 |
| atgacatatg | ccccactgtc | cataactcca | caacctggca | ttccgactat | aaggtcaaag | 600 |
| ggctatgtga | ttctaacctc | atttccacgg | acatcacctt | cttctcagag | gacagagagc | 660 |
| tatcatccct | aggaaaggag | ggcacagggt | tcagaagtaa | ctactttgct | tatgaaactg | 720 |
| gagacaaggc | ctgcaaaatg | cagtactgca | agcattgggg | agtcagactc | ccatcaggtg | 780 |
| tctggttcga | gatggctgat | aaggatctct | tgctgcagc | cagattccct | gaatgcccag | 840 |
| aagggtcaag | tatctctgct | ccatctcaga | cctcagtgga | tgtaagtctc | attcaggacg | 900 |
| ttgagaggat | cttggattat | tccctctgcc | aagaaacctg | gagcaaaatc | agagcgggtc | 960 |
| ttcccatctc | tccagtggat | ctcagctatc | ttgctcctaa | aaacccagga | accggtcctg | 1020 |
| cctttaccat | aatcaatggt | accctaaaat | actttgagac | cagatacatc | agagtcgata | 1080 |
| ttgctgctcc | aatcctctca | agaatggtcg | aatgatcag | tggaactacc | acagaaaggg | 1140 |
| aactgtggga | tgactgggct | ccatatgaag | acgtggaaat | tggacccaat | ggagttctga | 1200 |
| ggaccagttc | aggatataag | tttcctttat | atatgattgg | acatggtatg | ttggactccg | 1260 |
| gtcttcatct | tagctcaaag | gctcaggtgt | ttgaacatcc | tcacattcaa | gacgctgctt | 1320 |

```
cgcagcttcc tgatgatgag attttatttt ttggtgatac tgggctatcc aaaaatccaa    1380
tcgactttgt cgaaggttgg ttcagtagtt ggaagagctc cattgcctct ttttctttta    1440
tcatagggtt aatcattgga ctattcttgg ttctccgagt tggtatttat ctttacatta    1500
aattaaagca caccaagaaa agacagattt atacagacat agagatgaac cgacttggaa    1560
ggtaactcaa atcctgcaca acagattctt catgtttgga ccaaatcaac ttgtgatacc    1620
atgctcaaag aggcctcaat tatatttgag ttttttaattt ttatg                   1665
```

<210> SEQ ID NO 3
<211> LENGTH: 511
<212> TYPE: PRT
<213> ORGANISM: Vesicular stomatitis virus

<400> SEQUENCE: 3

```
Met Lys Cys Leu Leu Tyr Leu Ala Phe Leu Phe Ile Gly Val Asn Cys
 1               5                  10                  15

Lys Phe Thr Ile Val Phe Pro His Asn Gln Lys Gly Asn Trp Lys Asn
             20                  25                  30

Val Pro Ser Asn Tyr His Tyr Cys Pro Ser Ser Ser Asp Leu Asn Trp
         35                  40                  45

His Asn Asp Leu Ile Gly Thr Ala Leu Gln Val Lys Met Pro Lys Ser
     50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                 85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320
```

```
Leu Ala Pro Lys Asn Pro Gly Thr Gly Pro Ala Phe Thr Ile Ile Asn
            325                 330                 335
Gly Thr Leu Lys Tyr Phe Glu Thr Arg Tyr Ile Arg Val Asp Ile Ala
        340                 345                 350
Ala Pro Ile Leu Ser Arg Met Val Gly Met Ile Ser Gly Thr Thr Thr
    355                 360                 365
Glu Arg Glu Leu Trp Asp Asp Trp Ala Pro Tyr Glu Asp Val Glu Ile
370                 375                 380
Gly Pro Asn Gly Val Leu Arg Thr Ser Ser Gly Tyr Lys Phe Pro Leu
385                 390                 395                 400
Tyr Met Ile Gly His Gly Met Leu Asp Ser Asp Leu His Leu Ser Ser
                405                 410                 415
Lys Ala Gln Val Phe Glu His Pro His Ile Gln Asp Ala Ala Ser Gln
            420                 425                 430
Leu Pro Asp Asp Glu Ser Leu Phe Phe Gly Asp Thr Gly Leu Ser Lys
        435                 440                 445
Asn Pro Ile Glu Leu Val Glu Gly Trp Phe Ser Ser Trp Lys Ser Ser
    450                 455                 460
Ile Ala Ser Phe Phe Phe Ile Ile Gly Leu Ile Ile Gly Leu Phe Leu
465                 470                 475                 480
Val Leu Arg Val Gly Ile His Leu Cys Ile Lys Leu Lys His Thr Lys
                485                 490                 495
Lys Arg Gln Ile Tyr Thr Asp Ile Glu Met Asn Arg Leu Gly Lys
            500                 505                 510

<210> SEQ ID NO 4
<211> LENGTH: 1536
<212> TYPE: DNA
<213> ORGANISM: Vesicular stomatitis virus

<400> SEQUENCE: 4
atgaagtgcc ttttgtactt agcctttta ttcattgggg tgaattgcaa gttcaccata      60 gttttccac acaaccaaaa aggaaactgg aaaaatgttc cttctaatta ccattattgc     120
ccgtcaagct cagatttaaa ttggcataat gacttaatag cacagcctt acaagtcaaa     180 atgcccaaga gtcacaaggc tattcaagca gacggttgga tgtgtcatgc ttccaaatgg     240
gtcactactt gtgatttccg ctggtatgga ccgaagtata acacattc catccgatcc     300 ttcactccat ctgtagaaca atgcaaggaa agcattgaac aaacgaaaca aggaacttgg     360
ctgaatccag gcttccctcc tcaaagttgt ggatatgcaa ctgtgacgga tgccgaagca     420
gtgattgtcc aggtgactcc tcaccatgtg ctggttgatg aatacacagg agaatgggtt     480
gattcacagt tcatcaacgg aaaatgcagc aattacatat gccccactgt ccataactct     540
acaacctggc attctgacta taaggtcaaa gggctatgtg attctaacct catttccatg     600
gacatcacct tcttctcaga ggacggagag ctatcatccc tgggaaagga gggcacaggg     660
ttcagaagta actactttgc ttatgaaact ggaggcaagg cctgcaaaat gcaatactgc     720
aagcattggg gagtcagact cccatcaggt gtctggttcg agatggctga taaggatctc     780
tttgctgcag ccagattccc tgaatgccca gaagggcaa gtatctctgc tccatctcag     840
acctcagtgg atgtaagtct aattcaggac gttgagagga tcttggatta ttccctctgc     900
caagaaacct ggagcaaaat cagagcgggt cttccaatct ctccagtgga tctcagctat     960
cttgctccta aaaacccagg aaccggtcct gctttcacca taatcaatgg taccctaaaa    1020
tactttgaga ccagatacat cagagtcgat attgctgctc aatcctctc aagaatggtc    1080
```

-continued

```
ggaatgatca gtggaactac cacagaaagg gaactgtggg atgactgggc accatatgaa    1140
gacgtggaaa ttggacccaa tggagttctg aggaccagtt caggatataa gtttccttta    1200
tacatgattg acatggtat gttggactcc gatcttcatc ttagctcaaa ggctcaggtg     1260
ttcgaacatc ctcacattca agacgctgct tcgcaacttc ctgatgatga gagtttattt    1320
tttggtgata ctgggctatc caaaaatcca atcgagcttg tagaaggttg gttcagtagt    1380
tggaaaagct ctattgcctc ttttttcttt atcatagggt taatcattgg actattcttg    1440
gttctccgag ttggtatcca tctttgcatt aaattaaagc acaccaagaa aagacagatt    1500
tatacagaca tagagatgaa ccgacttgga aagtga                              1536
```

<210> SEQ ID NO 5
<211> LENGTH: 4
<212> TYPE: PRT
<213> ORGANISM: Artificial Sequence
<220> FEATURE:
<223> OTHER INFORMATION: synthetic linker

<400> SEQUENCE: 5

Ser Ser Gly Ser
 1

<210> SEQ ID NO 6
<211> LENGTH: 6
<212> TYPE: PRT
<213> ORGANISM: Artificial Sequence
<220> FEATURE:
<223> OTHER INFORMATION: synthetic linker

<400> SEQUENCE: 6

Gly Gly Ser Gly Gly Ser
 1               5

<210> SEQ ID NO 7
<211> LENGTH: 6
<212> TYPE: PRT
<213> ORGANISM: Artificial Sequence
<220> FEATURE:
<223> OTHER INFORMATION: synthetic linker

<400> SEQUENCE: 7

Ala Ala Ala Gly Gly Met
 1               5

<210> SEQ ID NO 8
<211> LENGTH: 14
<212> TYPE: PRT
<213> ORGANISM: Artificial Sequence
<220> FEATURE:
<223> OTHER INFORMATION: synthetic linker

<400> SEQUENCE: 8

Ala Ala Ala Gly Gly Met Pro Pro Ala Ala Ala Gly Gly Met
 1               5                  10

<210> SEQ ID NO 9
<211> LENGTH: 6
<212> TYPE: PRT
<213> ORGANISM: Artificial Sequence
<220> FEATURE:
<223> OTHER INFORMATION: synthetic linker

<400> SEQUENCE: 9

Ala Ala Ala Gly Gly Met
 1               5

-continued

```
<210> SEQ ID NO 10
<211> LENGTH: 8
<212> TYPE: PRT
<213> ORGANISM: Artificial Sequence
<220> FEATURE:
<223> OTHER INFORMATION: synthetic linker

<400> SEQUENCE: 10

Pro Pro Ala Ala Ala Gly Gly Met
1               5

<210> SEQ ID NO 11
<211> LENGTH: 16
<212> TYPE: PRT
<213> ORGANISM: Artificial Sequence
<220> FEATURE:
<223> OTHER INFORMATION: synthetic metal ion affinity peptide

<400> SEQUENCE: 11

His Leu Ile His Asn Val His Lys Glu Glu His Ala His Ala His Asn
1               5                   10                  15

<210> SEQ ID NO 12
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 12

Ser Ile Gly Tyr Pro Leu Pro
1               5

<210> SEQ ID NO 13
<211> LENGTH: 16
<212> TYPE: PRT
<213> ORGANISM: Artificial Sequence
<220> FEATURE:
<223> OTHER INFORMATION: synthetic targeting peptide

<400> SEQUENCE: 13

Gly His Ala Trp Arg Glu Pro Gly Arg Met Glu Leu Asn Gly Ala Ala
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 14

Gly Gly Gly Val Phe Trp Gln
1               5

<210> SEQ ID NO 15
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 15

His Gly Arg Val Arg Pro His
1               5
```

```
<210> SEQ ID NO 16
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 16

Val Val Leu Val Thr Ser Ser
 1               5

<210> SEQ ID NO 17
<211> LENGTH: 8
<212> TYPE: PRT
<213> ORGANISM: Artificial Sequence
<220> FEATURE:
<223> OTHER INFORMATION: synthetic targeting peptide

<400> SEQUENCE: 17

Cys Leu His Arg Gly Asn Ser Cys
 1               5

<210> SEQ ID NO 18
<211> LENGTH: 12
<212> TYPE: PRT
<213> ORGANISM: Artificial Sequence
<220> FEATURE:
<223> OTHER INFORMATION: synthetic targeting peptide

<400> SEQUENCE: 18

Cys Arg Ser Trp Asn Lys Ala Asp Asn Arg Ser Cys
 1               5                  10

<210> SEQ ID NO 19
<211> LENGTH: 6
<212> TYPE: PRT
<213> ORGANISM: Artificial Sequence
<220> FEATURE:
<223> OTHER INFORMATION: synthetic targeting peptide

<400> SEQUENCE: 19

Asn Gly Arg Ala His Ala
 1               5

<210> SEQ ID NO 20
<211> LENGTH: 9
<212> TYPE: PRT
<213> ORGANISM: Artificial Sequence
<220> FEATURE:
<223> OTHER INFORMATION: synthetic targeting peptide

<400> SEQUENCE: 20

Cys Asp Cys Arg Gly Asp Cys Phe Cys
 1               5

<210> SEQ ID NO 21
<211> LENGTH: 5
<212> TYPE: PRT
<213> ORGANISM: Artificial Sequence
<220> FEATURE:
<223> OTHER INFORMATION: synthetic targeting peptide

<400> SEQUENCE: 21

Cys Asn Gly Arg Cys
 1               5

<210> SEQ ID NO 22
<211> LENGTH: 13
```

-continued

```
<212> TYPE: PRT
<213> ORGANISM: Artificial Sequence
<220> FEATURE:
<223> OTHER INFORMATION: synthetic targeting peptide

<400> SEQUENCE: 22

Cys Asn Gly Arg Cys Val Ser Gly Cys Ala Gly Arg Cys
1               5                   10

<210> SEQ ID NO 23
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 23

Cys Gly Ser Leu Val Arg Cys
1               5

<210> SEQ ID NO 24
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 24

Pro Gly Pro Glu Gly Ala Gly
1               5

<210> SEQ ID NO 25
<211> LENGTH: 9
<212> TYPE: PRT
<213> ORGANISM: Artificial Sequence
<220> FEATURE:
<223> OTHER INFORMATION: synthetic targeting peptide

<400> SEQUENCE: 25

Cys Pro Gly Pro Glu Gly Ala Gly Cys
1               5

<210> SEQ ID NO 26
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 26

Gly Asn Lys Arg Thr Arg Gly
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic targeting peptide

<400> SEQUENCE: 27

Cys Gly Asn Lys Arg Thr Arg Gly Cys
1               5

<210> SEQ ID NO 28
<211> LENGTH: 9
<212> TYPE: PRT
<213> ORGANISM: Artificial Sequence
```

```
<220> FEATURE:
<223> OTHER INFORMATION: synthetic targeting peptide

<400> SEQUENCE: 28

Cys Val Leu Asn Gly Arg Met Glu Cys
 1               5

<210> SEQ ID NO 29
<211> LENGTH: 11
<212> TYPE: PRT
<213> ORGANISM: Artificial Sequence
<220> FEATURE:
<223> OTHER INFORMATION: synthetic targeting peptide

<400> SEQUENCE: 29

Gly Arg Gly Val Val Ser Ile Phe Lys Gly Val
 1               5                   10

<210> SEQ ID NO 30
<211> LENGTH: 7
<212> TYPE: PRT
<213> ORGANISM: Artificial Sequence
<220> FEATURE:
<223> OTHER INFORMATION: synthetic targeting peptide

<400> SEQUENCE: 30

Phe His Arg Arg Ile Lys Ala
 1               5

<210> SEQ ID NO 31
<211> LENGTH: 10
<212> TYPE: PRT
<213> ORGANISM: Artificial Sequence
<220> FEATURE:
<223> OTHER INFORMATION: synthetic targeting peptide

<400> SEQUENCE: 31

Lys Phe Asn Lys Pro Phe Val Phe Leu Ile
 1               5                   10

<210> SEQ ID NO 32
<211> LENGTH: 38
<212> TYPE: DNA
<213> ORGANISM: Artificial Sequence
<220> FEATURE:
<223> OTHER INFORMATION: chemically synthesized oligonucleotide

<400> SEQUENCE: 32
agtcgggccc accaccacca tcatcatggg gcccagtc                              38

<210> SEQ ID NO 33
<211> LENGTH: 38
<212> TYPE: DNA
<213> ORGANISM: Artificial Sequence
<220> FEATURE:
<223> OTHER INFORMATION: chemically synthesized oligonucleotide

<400> SEQUENCE: 33
gactgggccc catgatgatg gtggtggtgg gcccgact                              38

<210> SEQ ID NO 34
<211> LENGTH: 13
<212> TYPE: PRT
<213> ORGANISM: Artificial Sequence
<220> FEATURE:
<223> OTHER INFORMATION: artificial metal ion affinity peptide
<220> FEATURE:
<221> NAME/KEY: VARIANT
```

```
<222> LOCATION: 1, 2
<223> OTHER INFORMATION: Xaa = Any Amino Acid

<400> SEQUENCE: 34

Xaa Xaa Ala Ala His His His His His His Gly Ala Ala
 1               5                  10

<210> SEQ ID NO 35
<211> LENGTH: 39
<212> TYPE: DNA
<213> ORGANISM: Artificial Sequence
<220> FEATURE:
<223> OTHER INFORMATION: chemically synthesized oligonucleotide
<220> FEATURE:
<221> NAME/KEY: misc_feature
<222> LOCATION: 1, 2, 3, 4, 5
<223> OTHER INFORMATION: n = A,T,C or G

<400> SEQUENCE: 35
nnnnntgcgg cccaccacca ccatcatcat ggggccgca                              39

<210> SEQ ID NO 36
<211> LENGTH: 35
<212> TYPE: PRT
<213> ORGANISM: vesicular stomatitis virus G protein variant

<400> SEQUENCE: 36

Met Lys Cys Leu Leu Tyr Leu Ala Phe Leu Phe Ile Gly Val Asn Cys
 1               5                  10                  15

His His His His His His Lys Phe Thr Ile Val Phe Pro His Asn Gln
            20                  25                  30

Lys Gly Asn
        35

<210> SEQ ID NO 37
<211> LENGTH: 38
<212> TYPE: PRT
<213> ORGANISM: vesicular stomatitis virus G protein variant

<400> SEQUENCE: 37

Met Lys Cys Leu Leu Tyr Leu Ala Phe Leu Phe Ile Gly Val Asn Cys
 1               5                  10                  15

His His His His His His Gly Gly Ser Lys Phe Thr Ile Val Phe Pro
            20                  25                  30

His Asn Gln Lys Gly Asn
        35

<210> SEQ ID NO 38
<211> LENGTH: 41
<212> TYPE: PRT
<213> ORGANISM: vesicular stomatitis virus G protein variant

<400> SEQUENCE: 38

Met Lys Cys Leu Leu Tyr Leu Ala Phe Leu Phe Ile Gly Val Asn Cys
 1               5                  10                  15

His His His His His His Gly Gly Ser Gly Gly Ser Lys Phe Thr Ile
            20                  25                  30

Val Phe Pro His Asn Gln Lys Gly Asn
        35                  40

<210> SEQ ID NO 39
<211> LENGTH: 41
<212> TYPE: PRT
<213> ORGANISM: vesicular stomatitis virus G protein variant
```

```
<400> SEQUENCE: 39

Met Lys Cys Leu Leu Tyr Leu Ala Phe Leu Phe Ile Gly Val Asn Cys
1               5                   10                  15

Lys Phe Ser Gly Gly His His His His His His Gly Ser Thr Ile
            20                  25                  30

Val Phe Pro His Asn Gln Lys Gly Asn
        35                  40

<210> SEQ ID NO 40
<211> LENGTH: 35
<212> TYPE: PRT
<213> ORGANISM: vesicular stomatitis virus G protein variant

<400> SEQUENCE: 40

Met Lys Cys Leu Leu Tyr Leu Ala Phe Leu Phe Ile Gly Val Asn Cys
1               5                   10                  15

Lys Phe Thr Ile Val Phe Pro His His His His His His Asn Gln
            20                  25                  30

Lys Gly Asn
        35

<210> SEQ ID NO 41
<211> LENGTH: 41
<212> TYPE: PRT
<213> ORGANISM: vesicular stomatitis virus G protein variant

<400> SEQUENCE: 41

Met Lys Cys Leu Leu Tyr Leu Ala Phe Leu Phe Ile Gly Val Asn Cys
1               5                   10                  15

Lys Phe Thr Ile Val Phe Pro Ser Gly Gly His His His His His
            20                  25                  30

Gly Gly Ser His Asn Gln Lys Gly Asn
        35                  40

<210> SEQ ID NO 42
<211> LENGTH: 41
<212> TYPE: PRT
<213> ORGANISM: vesicular stomatitis virus G protein variant

<400> SEQUENCE: 42

Met Lys Cys Leu Leu Tyr Leu Ala Phe Leu Phe Ile Gly Val Asn Cys
1               5                   10                  15

Lys Phe Thr Ile Val Phe Pro His Ser Gly Gly His His His His
            20                  25                  30

His Gly Gly Ser Asn Gln Lys Gly Asn
        35                  40

<210> SEQ ID NO 43
<211> LENGTH: 41
<212> TYPE: PRT
<213> ORGANISM: vesicular stomatitis virus G protein variant

<400> SEQUENCE: 43

Met Lys Cys Leu Leu Tyr Leu Ala Phe Leu Phe Ile Gly Val Asn Cys
1               5                   10                  15

Lys Phe Thr Ile Val Phe Pro His Asn Ser Gly Gly His His His
            20                  25                  30

His His Gly Gly Ser Gln Lys Gly Asn
        35                  40
```

```
<210> SEQ ID NO 44
<211> LENGTH: 23
<212> TYPE: PRT
<213> ORGANISM: vesicular stomatitis virus G protein variant

<400> SEQUENCE: 44

Asp Tyr Lys Val Lys Ser Gly Gly His His His His His Gly Gly
 1               5                  10                  15

Ser Gly Leu Cys Asp Ser Asn
            20

<210> SEQ ID NO 45
<211> LENGTH: 40
<212> TYPE: PRT
<213> ORGANISM: vesicular stomatitis virus G protein variant

<400> SEQUENCE: 45

Met Lys Cys Leu Leu Tyr Leu Ala Phe Leu Phe Ile Gly Val Asn Cys
 1               5                  10                  15

Lys Phe Thr Ile Val Phe Pro His Asn Gln Lys Gly Asn Asp Tyr Lys
            20                  25                  30

Val Lys Gly Leu Cys Asp Ser Asn
            35                  40

<210> SEQ ID NO 46
<211> LENGTH: 28
<212> TYPE: PRT
<213> ORGANISM: Vesicular stomatitis virus G protein variant

<400> SEQUENCE: 46

Met Lys Cys Leu Leu Tyr Leu Ala Phe Leu Phe Ile Gly Val Asn Cys
 1               5                  10                  15

Lys Phe Thr Ile Val Phe Pro His Asn Gln Lys Gly
            20                  25

<210> SEQ ID NO 47
<211> LENGTH: 36
<212> TYPE: PRT
<213> ORGANISM: Vesicular stomatitis virus G protein variant

<400> SEQUENCE: 47

Met Lys Cys Leu Leu Tyr Leu Ala Phe Leu Phe Ile Gly Val Asn Cys
 1               5                  10                  15

Lys Phe Thr Ile Val Phe Pro Cys Gly Arg Gly Asp Ser Pro Cys His
            20                  25                  30

Asn Gln Lys Gly
        35

<210> SEQ ID NO 48
<211> LENGTH: 36
<212> TYPE: PRT
<213> ORGANISM: Vesicular stomatitis virus G protein variant

<400> SEQUENCE: 48

Met Lys Cys Leu Leu Tyr Leu Ala Phe Leu Phe Ile Gly Val Asn Cys
 1               5                  10                  15

Lys Phe Thr Ile Val Phe Pro Cys Gly Arg Gly Glu Ser Pro Cys His
            20                  25                  30

Asn Gln Lys Gly
        35
```

```
<210> SEQ ID NO 49
<211> LENGTH: 44
<212> TYPE: PRT
<213> ORGANISM: Vesicular stomatitis virus G protein variant

<400> SEQUENCE: 49

Met Lys Cys Leu Leu Tyr Leu Ala Phe Leu Phe Ile Gly Val Asn Cys
1               5                   10                  15

Lys Phe Thr Ile Val Phe Pro Cys Gln Ala Gly Thr Phe Ala Leu Arg
            20                  25                  30

Gly Asp Asn Pro Gln Gly Cys His Asn Gln Lys Gly
        35                  40

<210> SEQ ID NO 50
<211> LENGTH: 44
<212> TYPE: PRT
<213> ORGANISM: Vesicular stomatitis virus G protein variant

<400> SEQUENCE: 50

Met Lys Cys Leu Leu Tyr Leu Ala Phe Leu Phe Ile Gly Val Asn Cys
1               5                   10                  15

Lys Phe Thr Ile Val Phe Pro Cys Gln Ala Gly Thr Phe Ala Leu Arg
            20                  25                  30

Gly Glu Asn Pro Gln Gly Cys His Asn Gln Lys Gly
        35                  40

<210> SEQ ID NO 51
<211> LENGTH: 44
<212> TYPE: PRT
<213> ORGANISM: Vesicular stomatitis virus G protein variant

<400> SEQUENCE: 51

Met Lys Cys Leu Leu Tyr Leu Ala Phe Leu Phe Ile Gly Val Asn Cys
1               5                   10                  15

Lys Phe Thr Ile Val Phe Pro Cys Gln Gly Ala Thr Phe Ala Leu Arg
            20                  25                  30

Gly Asp Asn Pro Gln Gly Cys His Asn Gln Lys Gly
        35                  40

<210> SEQ ID NO 52
<211> LENGTH: 44
<212> TYPE: PRT
<213> ORGANISM: Vesicular stomatitis virus G protein variant

<400> SEQUENCE: 52

Met Lys Cys Leu Leu Tyr Leu Ala Phe Leu Phe Ile Gly Val Asn Cys
1               5                   10                  15

Lys Phe Thr Ile Val Phe Pro Cys Gln Gly Ala Thr Phe Ala Leu Arg
            20                  25                  30

Gly Glu Asn Pro Gln Gly Cys His Asn Gln Lys Gly
        35                  40
```